US 7,504,388 B2

United States Patent
Harats et al.

(10) Patent No.: US 7,504,388 B2
(45) Date of Patent: Mar. 17, 2009

(54) METHODS EMPLOYING AND COMPOSITIONS CONTAINING DEFINED OXIDIZED PHOSPHOLIPIDS FOR PREVENTION AND TREATMENT OF ATHEROSCLEROSIS

(75) Inventors: Dror Harats, Ramat Gan (IL); Jacob George, Tel Aviv (IL); Gideon Halperin, Jerusalem (IL); Niva Yacov, Tel-Aviv (IL); Eti Kovalevski-Ishai, Netania (IL)

(73) Assignee: Vascular Biogenics Ltd., Or Yehuda (IL)

( * ) Notice: Subject to any disclaimer, the term of this patent is extended or adjusted under 35 U.S.C. 154(b) by 411 days.

(21) Appl. No.: 11/183,884

(22) Filed: Jul. 19, 2005

(65) Prior Publication Data

US 2005/0272813 A1 Dec. 8, 2005

Related U.S. Application Data

(60) Division of application No. 10/718,596, filed on Nov. 24, 2003, now Pat. No. 7,186,704, which is a division of application No. 10/445,347, filed on May 27, 2003, now Pat. No. 6,838,452, which is a continuation-in-part of application No. PCT/IL01/01080, filed on Nov. 22, 2001.

(60) Provisional application No. 60/252,574, filed on Nov. 24, 2000.

(51) Int. Cl.
*A61K 31/66* (2006.01)

(52) U.S. Cl. .................. 514/114; 558/169; 558/170; 558/172

(58) Field of Classification Search ................. 514/114; 558/169, 170, 172

See application file for complete search history.

(56) References Cited

U.S. PATENT DOCUMENTS

2003/0225035 A1 12/2003 Harats et al.

2006/0194765 A1 8/2006 Garcia et al.
2007/0099868 A1 5/2007 Harats et al.

FOREIGN PATENT DOCUMENTS

JP 60-104066 6/1985
JP 07-258261 10/1995

OTHER PUBLICATIONS

Kern et al., 1998, CAS: 130:50286.*
Junius et al., 1990, CAS: 112:77856.*
Aono et al., 1998, CAS: 109:170803.*
Nitta et al., 1985, CAS: 102:4277.*
Macpherson et al., 1992, CAS: 117:68162.*
Wang et al., 1991, CAS: 114:40661.*
Karasawa et al., 1992, CAS:116:39343.*
Smal et al., 1989, CAS: 111:192750.*
Berchtold's, 1981, CAS: 95:42295.*
Smal et al., Molecular Immunology, (1989), 26(8), 711-19.*
Hoff et al. "Phospholipid Hydroxyaleknals: Biological and Chemical Properties of Specific Oxidized Lipids Present in Atherosclerotic Lesions", Arteriosclerosis, Thrombosis, and Vascular Biology, 23:275-282, 2003. p. 276, Fig. 1.
Podrez et al. "A Novel Family of Atherogenic Oxidized Phospholipids Promotes Macrophage Foam Cell Formation Via the Scavenger Receptor CD36 and Is Enriched in Atherosclerotic Lesions", The Journal of Biological Chemistry, 277(41): 38517-38523, 2002. Scheme 1 on p. 38519.
Podrez et al. "Identification of A Novel Family of Oxidized Phospholipids That Serve as Ligands for the Macrophage Scavenger Receptor CD36", The Journal of Biological Chemistry, 277(41): 38503-38516, 2002. Fig. 1, Table 1.
Subbanagounder et al. "Evidence That Phospholipid Oxidation Products and/or Platelet-Activating Factor Play an Important Role in Early Atherogenesis: In Vitro and In Vivo Inhibition by WEB 2086", Circulation Research, 85: 311-318, 1999, Compound 'PEIPC'.

* cited by examiner

*Primary Examiner*—Rei-tsang Shiao

(57) ABSTRACT

Novel synthetic forms of etherified oxidized phospholipids and methods of utilizing same for preventing and treating atherosclerosis and other related disorders, as well as inflammatory disorders, immune mediated diseases, autoimmune diseases and proliferative disorders, are provided. In addition, methods of synthesizing etherified and esterified oxidized phospholipids and of using same for preventing and treating atherosclerosis and other related disorders are also provided.

7 Claims, 8 Drawing Sheets

Compound I

Compound IIa  Compound IIb

Aortic Sinus Lesion ($\mu m^2$)

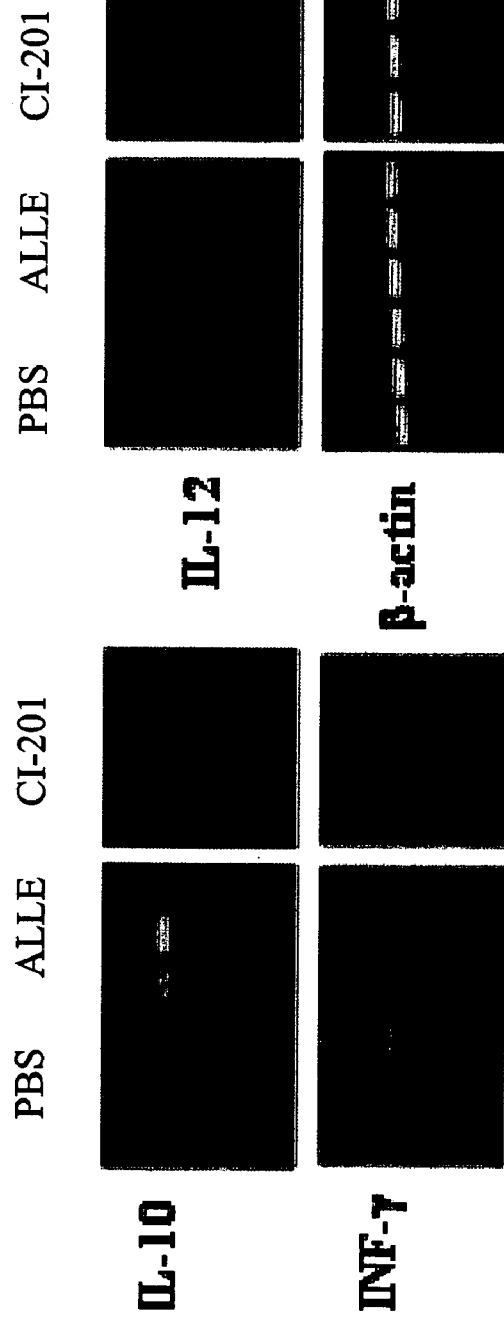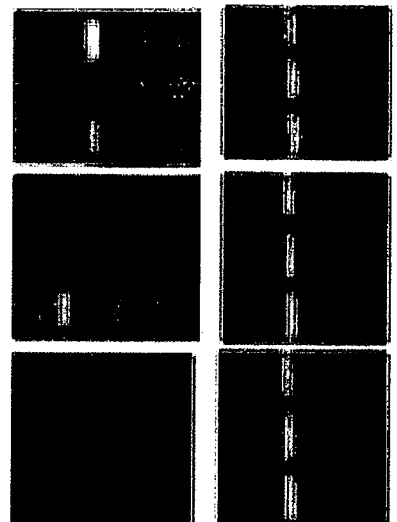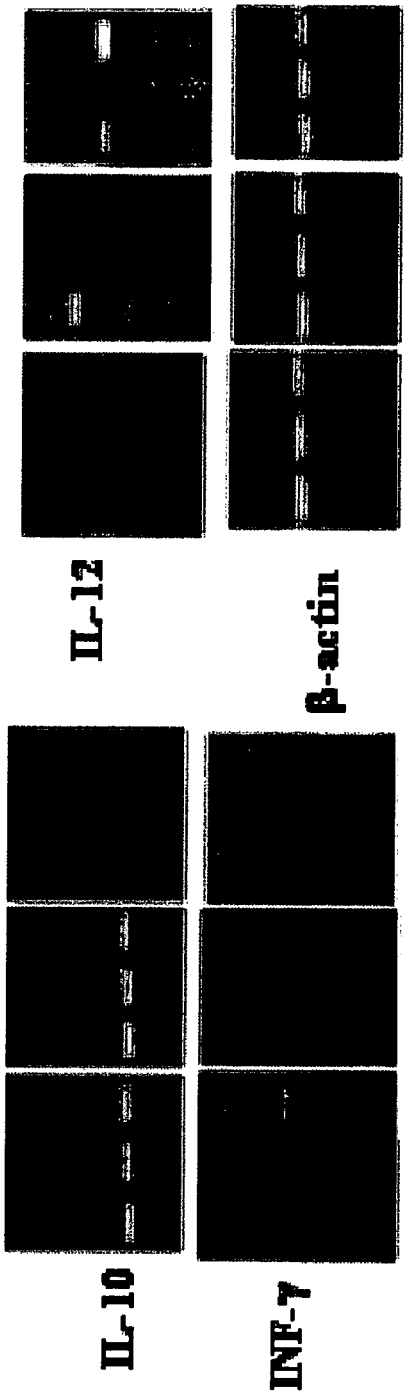
Fig. 12a
Fig. 12b
Fig. 12c
Fig. 12d

METHODS EMPLOYING AND COMPOSITIONS CONTAINING DEFINED OXIDIZED PHOSPHOLIPIDS FOR PREVENTION AND TREATMENT OF ATHEROSCLEROSIS

RELATED APPLICATIONS

This application is a divisional of U.S. patent application Ser. No. 10/718,596, filed on Nov. 24, 2003, now U.S. Pat. No. 7,186,704 which is a divisional of U.S. patent application Ser. No. 10/445,347, filed on May 27, 2003, now U.S. Pat. No. 6,838,452, issued on Jan. 4, 2005, which is a Continuation-In-Part (CIP) of PCT Patent Application No. PCT/IL01/01080, filed on Nov. 22, 2001, which claims the benefit of U.S. Provisional Patent Application No. 60/252,574, filed on Nov. 24, 2000.

FIELD AND BACKGROUND OF THE INVENTION

The present invention relates to defined, oxidized LDL (oxLDL) components for prevention and treatment of atherosclerosis and related diseases and disorders, as well as other inflammatory, immune mediated, autoimmune and proliferative diseases and disorders and, more particularly, to methods and compositions employing oxidized phospholipids effective in inducing mucosal tolerance and inhibiting inflammatory processes.

Cardiovascular disease is a major health risk throughout the industrialized world. Atherosclerosis, the most prevalent of cardiovascular diseases, is the principal cause of heart attack, stroke, and gangrene of the extremities, and as such, the principle cause of death in the United States. Atherosclerosis is a complex disease involving many cell types and molecular factors (for a detailed review, see Ross, 1993, Nature 362: 801-809). The process, which occurs in response to insults to the endothelium and smooth muscle cells (SMCs) of the wall of the artery, consists of the formation of fibrofatty and fibrous lesions or plaques, preceded and accompanied by inflammation. The advanced lesions of atherosclerosis may occlude the artery concerned, and result from an excessive inflammatory-fibroproliferative response to numerous different forms of insult. For example, shear stresses are thought to be responsible for the frequent occurrence of atherosclerotic plaques in regions of the circulatory system where turbulent blood flow occurs, such as branch points and irregular structures.

The first observable event in the formation of an atherosclerotic plaque occurs when inflammatory cells such as monocyte-derived macrophages adhere to the vascular endothelial layer and transmigrate through to the sub-endothelial space. Elevated plasma LDL levels lead to lipid engorgement of the vessel walls, with adjacent endothelial cells producing oxidized low density lipoprotein (LDL). In addition, lipoprotein entrapment by the extracellular matrix leads to progressive oxidation of LDL by lipoxygenases, reactive oxygen species, peroxynitrite and/or myeloperoxidase. These oxidized LDL's are then taken up in large amounts by vascular cells through scavenger receptors expressed on their surfaces.

Lipid-filled monocytes and smooth-muscle derived cells are called foam cells, and are the major constituent of the fatty streak. Interactions between foam cells and the endothelial and smooth muscle cells surrounding them produce a state of chronic local inflammation which can eventually lead to activation of endothelial cells, increased macrophage apoptosis, smooth muscle cell proliferation and migration, and the formation of a fibrous plaque (Hajjar, D P and Haberland, M E, J. Biol Chem, 1997 Sep. 12; 272(37):22975-78). Such plaques occlude the blood vessels concerned and thus restrict the flow of blood, resulting in ischemia, a condition characterized by a lack of oxygen supply in tissues of organs due to inadequate perfusion. When the involved arteries block the blood flow to the heart, a person is afflicted with a 'heart attack'; when the brain arteries occlude, the person experiences a stroke. When arteries to the limbs narrow, the result is severe pain, decreased physical mobility and possibly the need for amputation.

Oxidized LDL has been implicated in the pathogenesis of atherosclerosis and atherothrombosis, by its action on monocytes and smooth muscle cells, and by inducing endothelial cell apoptosis, impairing anticoagulant balance in the endothelium. Oxidized LDL also inhibits anti-atherogenic HDL-associated breakdown of oxidized phospholipids (Mertens, A and Holvoet, P, FASEB J 2001 October; 15(12):2073-84). This association is also supported by many studies demonstrating the presence of oxidized LDL in the plaques in various animal models of atherogenesis; the retardation of atherogenesis through inhibition of oxidation by pharmacological and/or genetic manipulations; and the promising results of intervention trials with anti-oxidant vitamins (see, for example, Witztum J and Steinberg, D, Trends Cardiovasc Med 2001 April-May; 11(3-4):93-102 for a review of current literature). Indeed, oxidized LDL and malondialdehyde (MDA)-modified LDL have been recently proposed as accurate blood markers for $1^{st}$ and $2^{nd}$ stages of coronary artery disease (U.S. Pat. No. 6,309,888 to Holvoet et. al. and U.S. Pat. No. 6,255,070 to Witztum, et al.).

Reduction of LDL oxidation and activity has been the target of a number of suggested clinical applications for treatment and prevention of cardiovascular disease. Bucala, et al. (U.S. Pat. No. 5,869,534) discloses methods for the modulation of lipid peroxidation by reducing advanced glycosylation end product, lipid characteristic of age-, disease- and diabetes-related foam cell formation. Tang et al., at Incyte Pharmaceuticals, Inc. (U.S. Pat. No. 5,945,308) have disclosed the identification and proposed clinical application of a Human Oxidized LDL Receptor in the treatment of cardiovascular and autoimmune diseases and cancer.

Atherosclerosis and Autoimmune Disease

Because of the presumed role of the excessive inflammatory-fibroproliferative response in atherosclerosis and ischemia, a growing number of researchers have attempted to define an autoimmune component of vascular injury. In autoimmune diseases the immune system recognizes and attacks normally non-antigenic body components (autoantigens), in addition to attacking invading foreign antigens. The autoimmune diseases are classified as auto- (or self-) antibody mediated or cell mediated diseases. Typical autoantibody mediated autoimmune diseases are myasthenia gravis and idiopathic thrombocytopenic purpura (ITP), while typical cell mediated diseases are Hashimoto's thyroiditis and type I (Juvenile) Diabetes.

The recognition that immune mediated processes prevail within atherosclerotic lesions stemmed from the consistent observation of lymphocytes and macrophages in the earliest stages, namely the fatty streaks. These lymphocytes which include a predominant population of CD4+ cells (the remainder being CD8+ cells) were found to be more abundant over macrophages in early lesions, as compared with the more advanced lesions, in which this ratio tends to reverse. These findings posed questions as to whether they reflect a primary immune sensitization to a possible antigen or alternatively stand as a mere epiphenomenon of a previously induced local tissue damage. Regardless of the factors responsible for the recruitment of these inflammatory cells to the early plaque, they seem to exhibit an activated state manifested by concomitant expression of MHC class II HLA-DR and interleukin (IL) receptor as well as leukocyte common antigen (CD45R0) and the very late antigen 1 (VLA-1) integrin.

The on-going inflammatory reaction in the early stages of the atherosclerotic lesion may either be the primary initiating event leading to the production of various cytokines by the local cells (i.e. endothelial cells, macrophages, smooth muscle cells and inflammatory cells), or it may be that this reaction is a form of the body's defense immune system towards the hazardous process. Some of the cytokines which have been shown to be upregulated by the resident cells include TNF-α, IL-1, IL-2, IL-6, IL-8, IFN-γ and monocyte chemoattractant peptide-1 (MCP-1). Platelet derived growth factor (PDGF) and insulin-like growth factor (ILGF) which are expressed by all cellular constituents within atherosclerotic plaques have also been shown to be overexpressed, thus possibly intensifying the preexisting inflammatory reaction by a co-stimulatory support in the form of a mitogenic and chemotactic factor. Recently, Uyemura et al. (Cross regulatory roles of IL-12 and IL-10 in atherosclerosis. J Clin Invest 1996 97; 2130-2138) have elucidated type 1 T-cell cytokine pattern in human atherosclerotic lesions exemplified by a strong expression of IFN-γ but not IL-4 mRNA in comparison with normal arteries. Furthermore, IL-12—a T-cell growth factor produced primarily by activated monocytes and a selective inducer of Th1 cytokine pattern, was found to be overexpressed within lesions as manifested by the abundance of its major heterodimer form p70 and p40 (its dominant inducible protein) mRNA.

Similar to the strong evidence for the dominance of the cellular immune system within the atherosclerotic plaque, there is also ample data supporting the involvement of the local humoral immune system. Thus, deposition of immunoglobulins and complement components have been shown in the plaques in addition to the enhanced expression of the C3b and C3Bi receptors in resident macrophages.

Valuable clues with regard to the contribution of immune mediated inflammation to the progression of atherosclerosis come from animal models. Immunocompromised mice (class I MHC deficient) tend to develop accelerated atherosclerosis as compared with immune competent mice. Additionally, treatment of C57BL/6 mice (Emeson E E, Shen M L. Accelerated atherosclerosis in hyperlipidemic C57BL/6 mice treated with cyclosporin A. Am J Pathol 1993; 142: 1906-1915) and New-Zealand White rabbits (Roselaar S E, Schonfeld G, Daugherty A. Enhanced development of atherosclerosis in cholesterol fed rabbits by suppression of cell mediated immunity. J Clin Invest 1995; 96: 1389-1394) with cyclosporin A, a potent suppressor of IL-2 transcription resulted in a significantly enhanced atherosclerosis under "normal" lipoprotein "burden". These latter studies may provide insight into the possible roles of the immune system in counteracting the self-perpetuating inflammatory process within the atherosclerotic plaque.

Atherosclerosis is not a classical autoimmune disease, although some of its manifestations such as the production of the plaque which obstructs the blood vessels may be related to aberrant immune responsiveness. In classical autoimmune disease, one can often define very clearly the sensitizing autoantigen attacked by the immune system and the component(s) of the immune system which recognize the autoantigen (humoral, i.e. autoantibody or cellular, i.e. lymphocytes). Above all, one can show that by passive transfer of these components of the immune system the disease can be induced in healthy animals, or in the case of humans the disease may be transferred from a sick pregnant mother to her offspring. Many of the above are not prevailing in atherosclerosis. In addition, the disease definitely has common risk factors such as hypertension, diabetes, lack of physical activity, smoking and others, the disease affects elderly people and has a different genetic preponderance than in classical autoimmune diseases.

Treatment of autoimmune inflammatory disease may be directed towards supression or reversal of general and/or disease-specific immune reactivity. Thus Aiello, for example (U.S. Pat. Nos. 6,034,102 and 6,114,395) discloses the use of estrogen-like compounds for treatment and prevention of atherosclerosis and atherosclerotic lesion progression by inhibition of inflammatory cell recruitment. Similarly, Medford et al. (U.S. Pat. No. 5,846,959) disclose methods for the prevention of formation of oxidized PUFA, for treatment of cardiovascular and non-cardiovascular inflammatory diseases mediated by the cellular adhesion molecule VCAM-1. Furthermore, Falb (U.S. Pat. No. 6,156,500) designates a number of cell signaling and adhesion molecules abundant in atherosclerotic plaque and disease as potential targets of anti-inflammatory therapies.

Since oxidized LDL has been clearly implicated in the pathogenesis of atherosclerosis (see above), the contribution of these prominent plaque components to autoimmunity in atheromatous disease processes has been investigated.

Immune Responsiveness to Oxidized LDL

It is known that oxidized LDL (Ox LDL) is chemotactic for T-cells and monocytes. Ox LDL and its byproducts are also known to induce the expression of factors such as monocyte chemotactic factor 1, secretion of colony stimulating factor and platelet activating properties, all of which are potent growth stimulants.

The active involvement of the cellular immune response in atherosclerosis has recently been substantiated by Stemme S., et al. (Proc Natl Acad Sci USA 1995; 92: 3893-97), who isolated CD4+ within plaques clones responding to Ox LDL as stimuli. The clones corresponding to Ox LDL (4 out of 27) produced principally interferon-γ rather than IL-4. It remains to be seen whether the above T-cell clones represent mere contact with the cellular immune system with the inciting strong immunogen (Ox LDL) or that this reaction provides means of combating the apparently indolent atherosclerotic process.

The data regarding the involvement of the humoral mechanisms and their meaning are much more controversial. One recent study reported increased levels of antibodies against MDA-LDL, a metabolite of LDL oxidation, in women suffering from heart disease and/or diabetes (Dotevall, et al., Clin Sci 2001 November; 101(5): 523-31). Other investigators have demonstrated antibodies recognizing multiple epitopes on the oxidized LDL, representing immune reactivity to the lipid and apolipoprotein components (Steinerova A., et al., Physiol Res 2001; 50(2): 131-41) in atherosclerosis and other diseases, such as diabetes, renovascular syndrome, uremia, rheumatic fever and lupus erythematosus. Several reports have associated increased levels of antibodies to Ox LDL with the progression of atherosclerosis (expressed by the degree of carotid stenosis, severity of peripheral vascular disease etc.). Most recently, Sherer et al. (Cardiology 2001; 95(1):20-4) demonstrated elevated levels of antibodies to cardiolipin, beta 2GPI and OxLDL, in coronary heart disease. Thus, there seems to be a consensus as to the presence of Ox LDL antibodies in the form of immune complexes within atherosclerotic plaque, although the true significance of this finding has not been established.

Antibodies to Ox LDL have been hypothesized as playing an active role in lipoprotein metabolism. Thus, it is known that immune complexes of Ox LDL and its corresponding antibodies are taken up more efficiently by macrophages in suspension as compared with Ox LDL. No conclusions can be drawn from this consistent finding on the pathogenesis of atherosclerosis since the question of whether the accelerated uptake of Ox LDL by the macrophages is beneficial or deleterious has not yet been resolved.

Important data as to the significance of the humoral immune system in atherogenesis comes from animal models. It has been found that hyperimmunization of LDL-receptor deficient rabbits with homologous oxidized LDL, resulted in the production of high levels of anti-Ox LDL antibodies and was associated with a significant reduction in the extent of atherosclerotic lesions as compared with a control group exposed to phopsphate-buffered saline (PBS). A decrease in plaque formation has also been accomplished by immunization of rabbits with cholesterol rich liposomes with the concomitant production of anti-cholesterol antibodies, yet this effect was accompanied by a 35% reduction in very low density lipoprotein cholesterol levels.

Thus, both the pathogenic role of oxidized LDL components and their importance as autoantigens in atherosclerosis, as well as other diseases, have been extensively demonstrated in laboratory and clinical studies.

Mucosal Tolerance in Treatment of Autoimmune Disease

Recently, new methods and pharmaceutical formulations have been found that are useful for treating autoimmune diseases (and related T-cell mediated inflammatory disorders such as allograft rejection and retroviral-associated neurological disease). These treatments induce tolerance, orally or mucosally, e.g. by inhalation, using as tolerizers autoantigens, bystander antigens, or disease-suppressive fragments or analogs of autoantigens or bystander antigens. Such treatments are described, for example, in U.S. Pat. No. 5,935,577 to Weiner et al. Autoantigens and bystander antigens are defined below (for a general review of mucosal tolerance see Nagler-Anderson, C., Crit Rev Immunol 2000; 20(2):103-20). Intravenous administration of autoantigens (and fragments thereof containing immunodominant epitopic regions of their molecules) has been found to induce immune suppression through a mechanism called clonal anergy. Clonal anergy causes deactivation of only immune attack T-cells specific to a particular antigen, the result being a significant reduction in the immune response to this antigen. Thus, the autoimmune response-promoting T-cells specific to an autoantigen, once anergized, no longer proliferate in response to that antigen. This reduction in proliferation also reduces the immune reactions responsible for autoimmune disease symptoms (such as neural tissue damage that is observed in MS). There is also evidence that oral administration of autoantigens (or immunodominant fragments) in a single dose and in substantially larger amounts than those that trigger "active suppression" may also induce tolerance through anergy (or clonal deletion).

A method of treatment has also been disclosed that proceeds by active suppression. Active suppression functions via a different mechanism from that of clonal anergy. This method, discussed extensively in PCT Application PCT/US93/01705, involves oral or mucosal administration of antigens specific to the tissue under autoimmune attack. These are called "bystander antigens". This treatment causes regulatory (suppressor) T-cells to be induced in the gut-associated lymphoid tissue (GALT), or bronchial associated lymphoid tissue (BALT), or most generally, mucosa associated lymphoid tissue (MALT) (MALT includes GALT and BALT). These regulatory cells are released in the blood or lymphatic tissue and then migrate to the organ or tissue afflicted by the autoimmune disease and suppress autoimmune attack of the afflicted organ or tissue. The T-cells elicited by the bystander antigen (which recognize at least one antigenic determinant of the bystander antigen used to elicit them) are targeted to the locus of autoimmune attack where they mediate the local release of certain immunomodulatory factors and cytokines, such as transforming growth factor beta (TGF-$\beta$), interleukin-4 (IL-4), and/or interleukin-10 (IL-10). Of these, TGF-$\beta$ is an antigen-nonspecific immunosuppressive factor in that it suppresses immune attack regardless of the antigen that triggers the attack. (However, because oral or mucosal tolerization with a bystander antigen only causes the release of TGF-$\beta$ in the vicinity of autoimmune attack, no systemic immunosuppression ensues.) IL-4 and IL-10 are also antigen-nonspecific immunoregulatory cytokines. IL-4 in particular enhances (T helper $Th_2$) $Th_2$ response, i.e., acts on T-cell precursors and causes them to differentiate preferentially into $Th_2$ cells at the expense of $Th_1$ responses. IL-4 also indirectly inhibits $Th_1$ exacerbation. IL-10 is a direct inhibitor of $Th_1$ responses. After orally tolerizing mammals afflicted with autoimmune disease conditions with bystander antigens, increased levels of TGF-$\beta$, IL-4 and IL-10 are observed at the locus of autoimmune attack (Chen, Y. et al., Science, 265: 1237-1240, 1994). The bystander suppression mechanism has been confirmed by von Herreth et al., (J. Clin. Invest., 96:1324-1331, September 1996).

More recently, oral tolerance has been effectively applied in treatment of animal models of inflammatory bowel disease by feeding probiotic bacteria (Dunne, C, et al., Antonie Van Leeuwenhoek 1999 July-November; 76(1-4):279-92), autoimmune glomerulonephritis by feeding glomerular basement membrane (Reynolds, J. et al., J Am Soc Nephrol 2001 January; 12(1): 61-70) experimental allergic encephalomyelitis (EAE, which is the equivalent of multiple sclerosis or MS), by feeding myelin basic protein (MBP), adjuvant arthritis and collagen arthritis, by feeding a subject with collagen and HSP-65, respectively. A Boston based company called Autoimmune has carried out several human experiments for preventing diabetes, multiple sclerosis, rheumatoid arthritis and uveitis. The results of the human experiments have been less impressive than the non-human ones, however there has been some success with the prevention of arthritis.

Oral tolerance to autoantigens found in atherosclerotic plaque lesions has also been investigated. Study of the epitopes recognized by T-cells and Ig titers in clinical and experimental models of atherosclerosis indicated three candidate antigens for suppression of inflammation in atheromatous lesions: oxidized LDL, the stress-related heat shock protein HSP 65 and the cardiolipin binding protein beta 2GP1. U.S. patent application Ser. No. 09/806,400 to Shoenfeld et al. (filed Sep. 30, 1999), which is incorporated herein in its entirety, discloses the reduction by approximately 30% of atherogenesis in the arteries of genetically susceptible LDL-RD receptor deficient transgenic mice fed with oxidized human LDL. This protective effect, however, was achieved by feeding a crude antigen preparation consisting of centrifuged, filtered and purified human serum LDL which had been subjected to a lengthy oxidation process with $Cu^{++}$. Although significant inhibition of atherogenesis was achieved, presumably via oral tolerance, no identification of specific lipid antigens or immunogenic LDL components was made. Another obstacle encountered was the inherent instability of the crude oxidized LDL in vivo, due to enzymatic activity and uptake of oxidized LDL by the liver and cellular immune mechanisms. It is plausible that a stable, more carefully defined oxidized LDL analog would have provided oral tolerance of greater efficiency.

The induction of immune tolerance and subsequent prevention or inhibition of autoimmune inflammatory processes has been demonstrated using exposure to suppressive antigens via mucosal sites other than the gut. The membranous tissue around the eyes, and the mucosa of the nasal cavity, as well as the gut, are exposed to many invading as well as self-antigens and possess mechanisms for immune reactivity. Thus, Rossi, et al. (Scand J Immunol 1999 August; 50(2):177-82) found that nasal administration of gliadin was as effective as intravenous administration in downregulating the immune response to the antigen in a mouse model of celiac disease. Similarly, nasal exposure to acetylcholine receptor antigen was more effective than oral exposure in delaying and reducing muscle weakness and specific lymphocyte proliferation in a mouse model of myasthenia gravis (Shi, F D. et al., J Immunol 1999 May 15; 162 (10): 5757-63). Therefore, immunogenic compounds intended for mucosal as well as intravenous or intraperitoneal administration should optimally be adaptable to nasal and other membranous routes of administration.

Thus, there is clearly a need for novel, well defined, synthetic oxidized phospholipid derivatives exhibiting enhanced metabolic stability and efficient tolerizing immunogenicity in intravenous, intraperitoneal and mucosal administration.

Synthesis of Oxidized Phospholipids

Modification of phospholipids has been employed for a variety of applications. For example, phospholipids bearing lipid-soluble active compounds may be incorporated into compositions for trans-dermal and trans-membranal application (U.S. Pat. No. 5,985,292 to Foumerou et al.) and phospholipid derivatives can be incorporated into liposomes and biovectors for drug delivery (see, for example, U.S. Pat. Nos. 6,261,597 and 6,017,513 to Kurtz and Betbeder, et al., respectively, and U.S. Pat. No. 4,614,796). U.S. Pat. No. 5,660,855 discloses lipid constructs of aminomannose derivatized cholesterol suitable for targeting smooth muscle cells or tissue, formulated in liposomes. These formulations are aimed at reducing restenosis in arteries, using PTCA procedures. The use of liposomes for treating atherosclerosis has been further disclosed in WO 95/23592, to Hope and Rodrigueza, who teach pharmaceutical compositions of unilamellar liposomes that may contain phospholipids. The liposomes disclosed in WO 95/23592 are aimed at optimizing cholesterol efflux from atherosclerotic plaque and are typically non-oxidized phospholipids.

Modified phospholipid derivatives mimicking platelet activation factor (PAF) structure are known to be pharmaceutically active in variety of disorders and diseases, effecting such functions as vascular permeability, blood pressure, heart function inhibition etc. It has been suggested that one group of these derivatives may have anti cancerous activity (U.S. Pat. No. 4,778,912 to Inoue at al.). However, the compound disclosed in U.S. Pat. No. 4,778,912 possesses a much longer bridge between the phosphate and the tertiary amine moiety than in the phosphatidyl group and therefore is not expected to be immunologically similar to Ox LDL. U.S. Pat. No. 4,329,302 teaches synthetic phosphoglycerides compounds—lysolechitin derivatives—that are usable in mediating platelet activation. While the compounds disclosed in U.S. Pat. No. 4,329,302 are either 1-O-alkyl ether or 1-O-fatty acyl phosphoglycerides, it was found that small chain acylation of lysolechitin gave rise to compounds with platelet activating behaviour, as opposed to long-chain acylation, and that the 1-O-alkyl ether are biologically superior to the corresponding 1-O-fatty acyl derivatives in mimicking PAF.

The structural effect of various phospholipids on the biological activity thereof has also been investigated by Tokumura et al. (Journal of Pharmacology and Experimental Therapeutics. July 1981, Vol. 219, No. 1) and in U.S. Pat. No. 4,827,011 to Wissner et al., with respect to hypertension.

Another group of modified phospholipid ether derivatives has been disclosed which was intended for chromatographic separation, but might have some physiological effect (CH Pat. No. 642,665 to Berchtold).

Oxidation of phospholipids occurs in vivo through the action of free radicals and enzymatic reactions abundant in atheromatous plaque. In vitro, preparation of oxidized phospholipids usually involves simple chemical oxidation of a native LDL or LDL phospholipid component. Investigators studying the role of oxidized LDL have employed, for example, ferrous ions and ascorbic acid (Itabe, H., et al., J. Biol. Chem. 1996; 271:33208-217) and copper sulfate (George, J. et al., Atherosclerosis. 1998; 138:147-152; Ameli, S. et al., Arteriosclerosis Thromb Vasc Biol 1996; 16:1074-79) to produce oxidized, or mildly oxidized phospholipid molecules similar to those associated with plaque components. Similarly prepared molecules have been shown to be identical to auto-antigens associated with atherogenesis (Watson A. D. et al., J. Biol. Chem. 1997; 272:13597-607) and able to induce protective anti-atherogenic immune tolerance (U.S. patent application Ser. No. 09/806,400 to Shoenfeld et al., filed Sep. 30, 1999) in mice. Likewise, Koike (U.S. Pat. No. 5,561,052) discloses a method of producing oxidized lipids and phospholipids using copper sulfate and superoxide dismutase to produce oxidized arachidonic or linoleic acids and oxidized LDL for diagnostic use. Davies et al. (J. Biol. Chem. 2001, 276:16015) teach the use of oxidized phospholipids as peroxisome proliferator-activated receptor agonists.

1-Palmitoyl-2-(5-oxovaleroyl)-sn-glycero-3-phosphocholine (POVPC, see Example I for a 2-D structural description) and derivatives thereof such as 1-palmitoyl-2-glutaroyl-sn-glycero-3-phosphocholine (PGPC) are representative examples of mildly oxidized esterified phospholipids that have been studied with respect to atherogenesis (see, for example, Boullier et al., J. Biol. Chem. 2000, 275:9163; Subbanagounder et al., Circulation Research, 1999, pp. 311). The effect of different structural analogs that belong to this class of oxidized phospholipids has also been studied (see, for example, Subbanagounder et al., Arterioscler. Thromb. Nasc. Biol. 2000, pp. 2248; Leitinger et al., Proc. Nat. Ac. Sci. 1999, 96:12010).

However, in vivo applications employing oxidized phospholipids prepared as above have the disadvantage of susceptibility to recognition, binding and metabolism of the active component in the body, making dosage and stability after administration an important consideration.

Furthermore, the oxidation techniques employed are non-specific, yielding a variety of oxidized products, necessitating either further purification or use of impure antigenic compounds. This is of even greater concern with native LDL, even if purified.

Thus, there is a widely recognized need for, and it would be highly advantageous to have, a novel, synthetic oxidized phospholipid and improved methods of synthesis and use thereof devoid of the above limitations.

SUMMARY OF THE INVENTION

According to the present invention there is provided a compound having a formula:

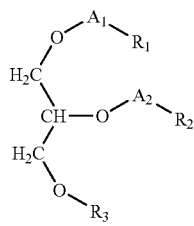

or pharmaceutically acceptable salts thereof, wherein:
(i) $A_1$ and $A_2$ are each independently selected from the group consisting of $CH_2$ and $C=O$, at least one of $A_1$ and $A_2$ being $CH_2$;
(ii) $R_1$ and $R_2$ are each independently selected from the group consisting of an alkyl chain having 1-27 carbon atoms and

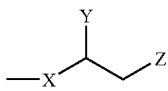

wherein X is an alkyl chain having 1-14 carbon atoms, Y is selected from the group consisting of:

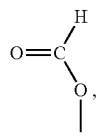

—OH, —H, alkyl, alkoxy, halogen, acetoxy and aromatic functional groups; and
Z is selected from the group consisting of:

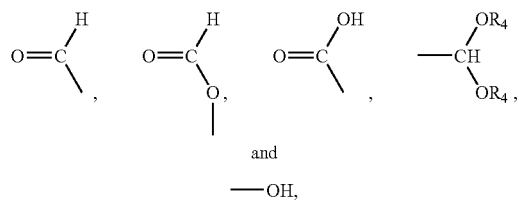

where as $R_4$ is an alkyl,
at least one of $R_1$ and $R_2$ being

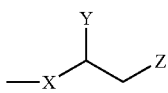

as described above; and
(iii) $R_3$ is selected from the group consisting of H, acyl, alkyl, phosphatidyl choline, phosphatidyl ethanolamine, phosphatidyl serine, phosphatidyl cardiolipin and phosphatidyl inisitol.

According to further features in the preferred embodiments of the is invention described below, $R_3$ is a non-phosphatidyl moeity, and as such the compound is a diglyceride.

According to still further features in the described preferred embodiments each of $A_1$ and $A_2$ is $CH_2$.

According to still further features in the described preferred embodiments $R_1$ is an alkyl chain having 1-27 carbon atoms and $R_2$ is

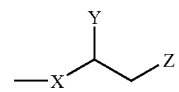

as described hereinabove.

According to another aspect of the present invention there is provided a pharmaceutical composition for prevention and/or treatment of atherosclerosis, cardiovascular disorders, cerebrovascular disorders, peripheral vascular disease, stenosis, restenosis and/or in-stent-stenosis in a subject in need thereof, the composition comprising, as an active ingredient, a therapeutically effective amount of the compound described hereinabove and a pharmaceutically acceptable carrier.

According to further features in preferred embodiments of the invention described below, the pharmaceutical composition is packaged and identified for use in the prevention and/or treatment of at least one disorder selected from the group consisting of atherosclerosis, cardiovascular disorders, cerebrovascular disease, peripheral vascular disorders, stenosis, restenosis and/or in-stent-stenosis.

According to yet another aspect of the present invention there is provided a pharmaceutical composition for prevention and/or treatment of an inflammatory disorder, an immune mediated disease, an autoimmune disease and a proliferative disorder selected from the group consisting of aging, rheumatoid arthritis, juvenile rheumatoid arthritis, inflammatory bowl disease and cancer in a subject in need thereof, comprising, as an active ingredient, a therapeutically effective amount of the compound described hereinabove and a pharmaceutically acceptable carrier.

According to further features in preferred embodiments of the invention described below, the pharmaceutical composition is packaged and identified for use in the prevention and/or treatment of an inflammatory disorder, an immune mediated disease, an autoimmune disease and a proliferative disorder selected from the group consisting of aging, rheumatoid arthritis, juvenile rheumatoid arthritis, inflammatory bowl disease and cancer.

According to yet further features in preferred embodiments of the invention described below, each of the pharmaceutical compositions described above is designed for inducing tolerance to oxidized LDL via mucosal administration.

According to further features in preferred embodiments of the invention described below, each of the pharmaceutical compositions described above is designed for nasal, oral, subcutaneous or intra-peritoneal administration, alone or in combination with additional routes of immunomodulation.

According to still further features in preferred embodiments of the invention described below, the compound reduces immune reactivity to oxidized LDL in the subject.

According to still further features in preferred embodiments of the invention described below, each of the pharmaceutical compositions described above further comprises a therapeutically effective amount of at least one additional compound selected from the group consisting of HMG CoA reductase inhibitors (Statins) mucosal adjuvants, corticosteroids, anti-inflammatory compounds, analgesics, growth factors, toxins, and additional tolerizing antigens.

According to still another aspect of the present invention there is provided a pharmaceutical composition for prevention and/or treatment of a disease, syndrome or condition selected from the group consisting of atherosclerosis, cardiovascular disorders, cerebrovascular disorders, peripheral vascular disease, stenosis, restenosis and/or in-stent-stenosis in a subject in need thereof, comprising, as an active ingredient, a therapeutically effective amount of a synthetic LDL derivative, or pharmaceutically acceptable salts thereof, the composition further comprising a pharmaceutically acceptable carrier.

According to an additional aspect of the present invention there is provided a method of prevention and/or treatment of atherosclerosis, cardiovascular disease, cerebrovascular disease, peripheral vascular disease, stenosis, restenosis and/or in-stent-stenosis in a subject in need thereof, the method comprising administering a therapeutically effective amount of the compound of the present invention as described hereinabove.

According to yet an additional aspect of the present invention there is provided a method of prevention and/or treatment of an inflammatory disorder, an immune mediated disease, an autoimmune disease and a proliferative disorder selected from the group consisting of aging, rheumatoid arthritis, juvenile rheumatoid arthritis, inflammatory bowl disease and cancer in a subject in need thereof, the method comprising administering a therapeutically effective amount of the compound of the present invention as described hereinabove.

According to yet further features in preferred embodiments of the invention described below, the compound is administered via mucosal administration.

According to further features in preferred embodiments of the invention described below, the administration of the compound is nasal, oral, subcutaneous or intra-peritoneal administration, alone or in combination with additional routes of immunomodulation.

According to still further features in preferred embodiments of the invention described below, the administration of the compound reduces immune reactivity to oxidized LDL in the subject.

According to further features in preferred embodiments of the invention described below, the compound is administered in addition to a therapeutically effective amount of at least one additional compound selected from the group consisting of HMG CoA reductase inhibitors (Statins), mucosal adjuvants, corticosteroids, anti-inflammatory compounds, analgetics, growth factors, toxins, and additional tolerizing antigens.

According to still further features in preferred embodiments of the invention described below, preferred compounds that are usable in the context of the present invention include 1-hexadecyl-2-(5'-oxo-pentanyl)-sn-glycero-3-phosphocholine (D-ALLE), 3-hexadecyl-2-(5'-oxo-pentanyl)-sn-glycero-1-phosphocholine (L-ALLE) and racemic mixtures thereof; 1-hexadecyl-2-(5'-carboxy-butyl)-sn-glycero-3-phosphocholine (CI-201) and its corresponding acetals and any combination of the above.

According to yet a further aspect of the present invention there is provided a method of synthesizing an oxidized phospholipid, the method comprising: (a) providing a phospholipid backbone including two fatty acid side chains, wherein at least one of the fatty acid side chains is a mono-unsaturated fatty acid; and (b) oxidizing the unsaturated bond of the mono-unsaturated fatty acid to thereby generate the oxidized phospholipid.

According to further features in preferred embodiments of the invention described below the phospholipid backbone further includes a moiety selected from the group consisting of H, acyl, alkyl, phosphatidyl choline, phosphatidyl ethanolamine, phosphatidyl serine, phosphatidyl cardiolipin and phosphatidyl inositol.

According to still further features in preferred embodiments of the invention described below the mono unsaturated fatty acid is $C_{2-15}$.

According to yet further features in preferred embodiments of the invention described below the oxidized phospholipid is 1-palmitoyl-2-oxovaleroyl-sn-glycero-3-phosphocholine, (POVPC), and the mono-unsaturated fatty acid is 5-hexenoic acid.

The present invention successfully addresses the shortcomings of the presently known configurations by providing novel synthetic oxidized LDL derivatives and methods of inducing immune tolerance to oxidized LDL utilizing same, as well as a novel approach of synthesizing oxidized LDL derivatives.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

Figure 5:
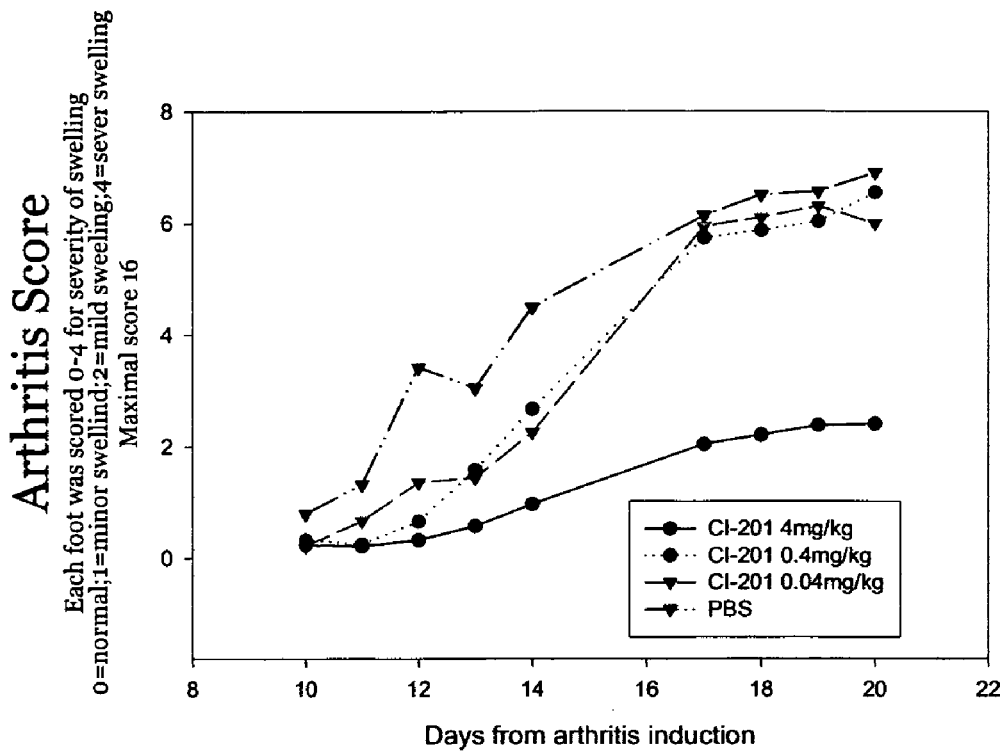
Figure 6:
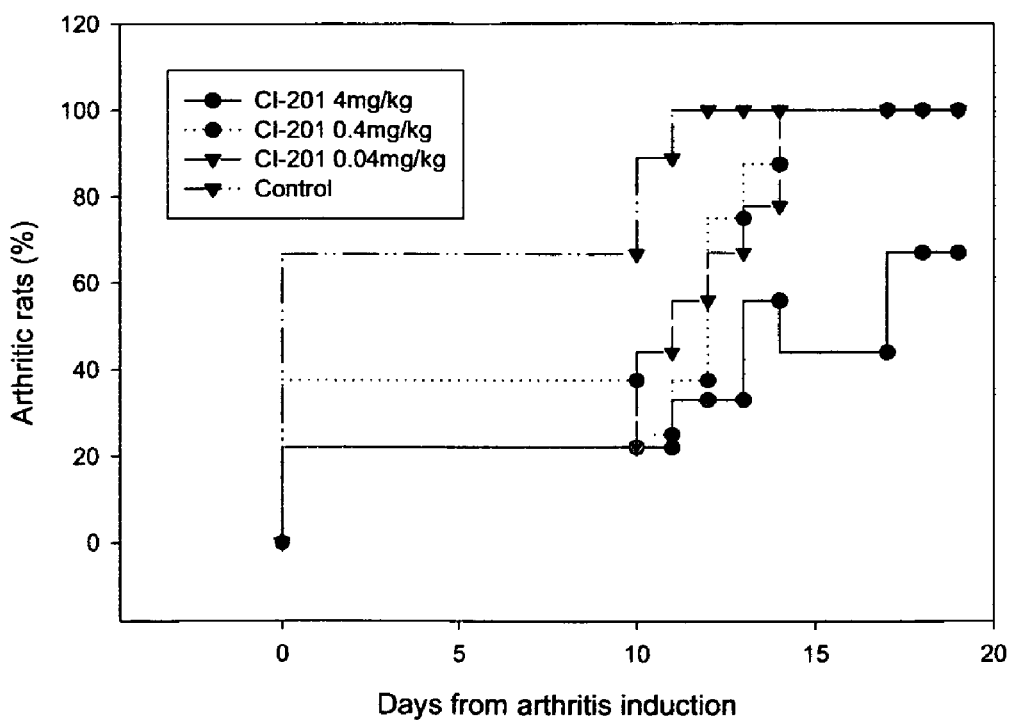

µg/mouse (ALLE L+D 10 µg) (n=11) or 1 mg/mouse (ALLE L+D 1 mg) (n=11); or PBS (CONTROL) (n=12) every other day for 5 days. Atherogenesis is expressed as the area of atheromatous lesions in the aortic sinus 8 weeks after the last feeding;

FIG. 5 is a graphic representation demonstrating inhibition of early atherogenesis in apoE-knock out mice by mucosal tolerance induced by oral feeding L-ALLE. 7-10 week old apo-E knock out mice were either fed 1 mg/mouse L-ALLE every other day for 5 days (OT L-ALLE) (n=11) or intranasally administered with 10 µg/mouse L-ALLE every other day for 3 days (NT L-ALLE) (n=11). Control mice were fed an identical volume (0.2 ml) of PBS (PBS ORAL) (n=12). Atherogenesis is expressed as the area of atheromatous lesions in the aortic sinus 8 weeks after the last oral or nasal exposure;

FIG. 6 is a graphic representation demonstrating suppression of immune reactivity to atheroslerotic plaque antigens induced by oral feeding with the synthetic oxidized phospholipids L-ALLE and POVPC. 6 week old male apo-E mice were fed either 1 mg/mouse L-ALLE (L-ALLE) (n=2) or POVPC (POVPC) (n=3) in 0.2 ml PBS; or PBS alone (CONTROL) (n=3) every other day for 5 days. One week following the last feeding the mice were immunized with a single subcutaneous injection of 50 µg Human oxidized LDL antigen. 7 days later T-cells from inguinal lymph node were prepared as described in Materials and Methods section that follows, and exposed to the sensitizing Human ox-LDL antigen for in-vitro assessment of proliferation. Proliferation, indicating immune reactivity, is expressed as the ratio between incorporation of labeled thymidine into the T-cell's DNA in the presence and absence of human ox-LDL antigen (stimulation index, S.I.).

Figure 7:
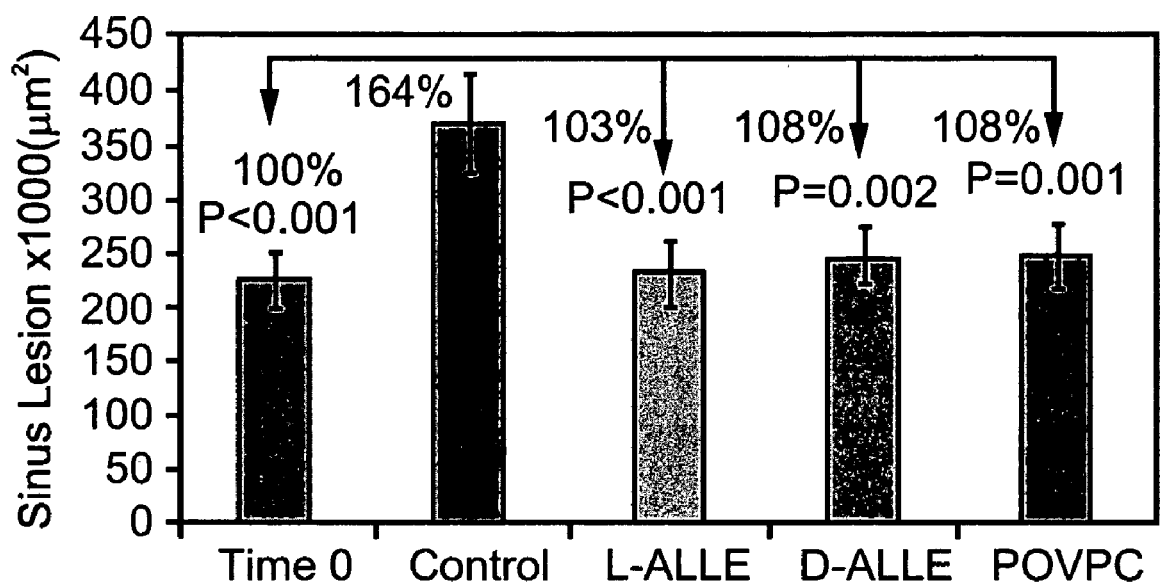
Figure 8:
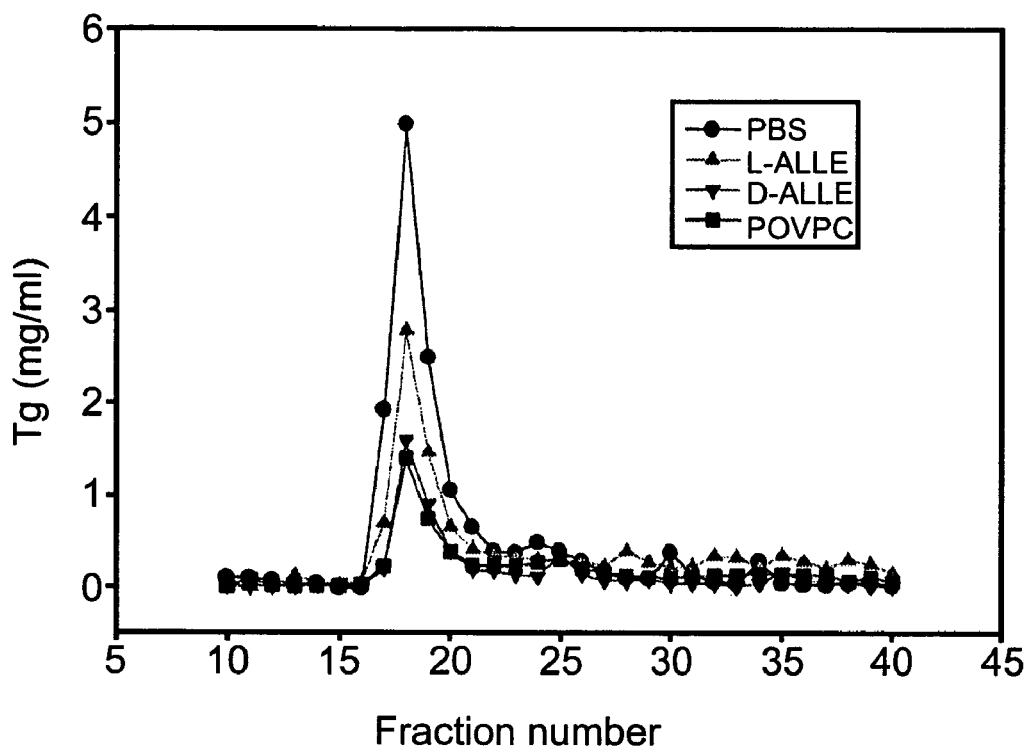
Figure 9:
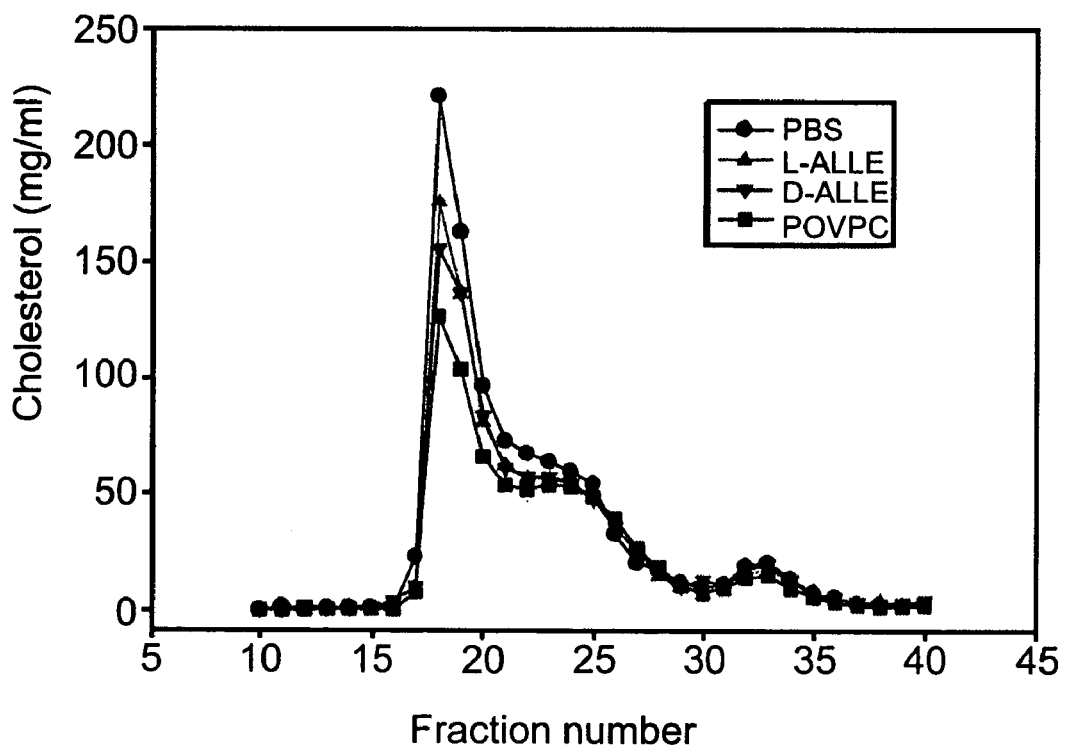
Figure 10:
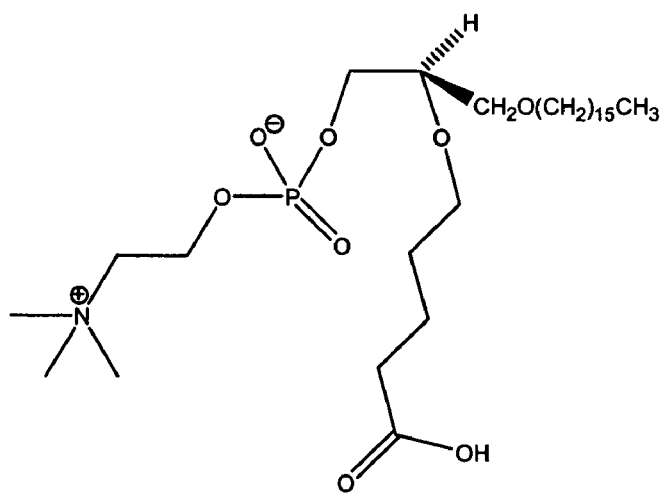
Figure 10:
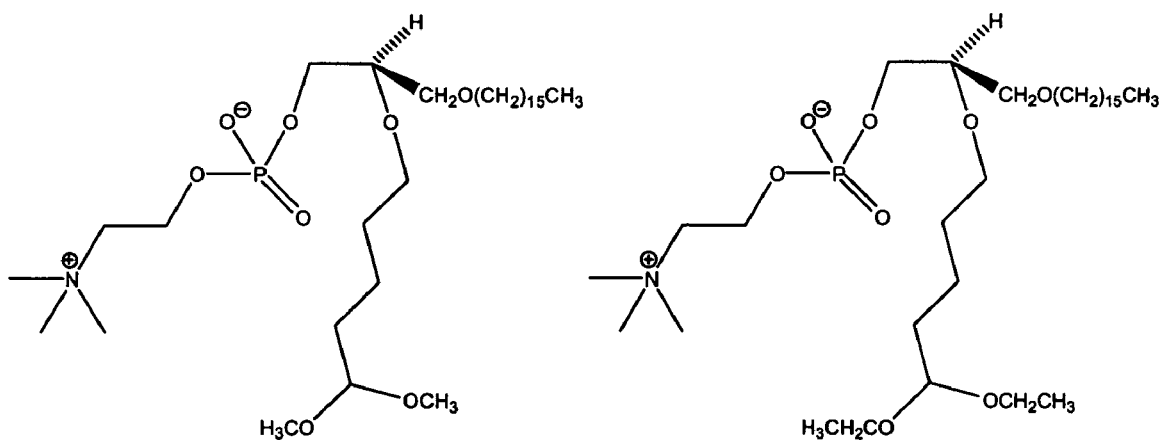
Figure 11:
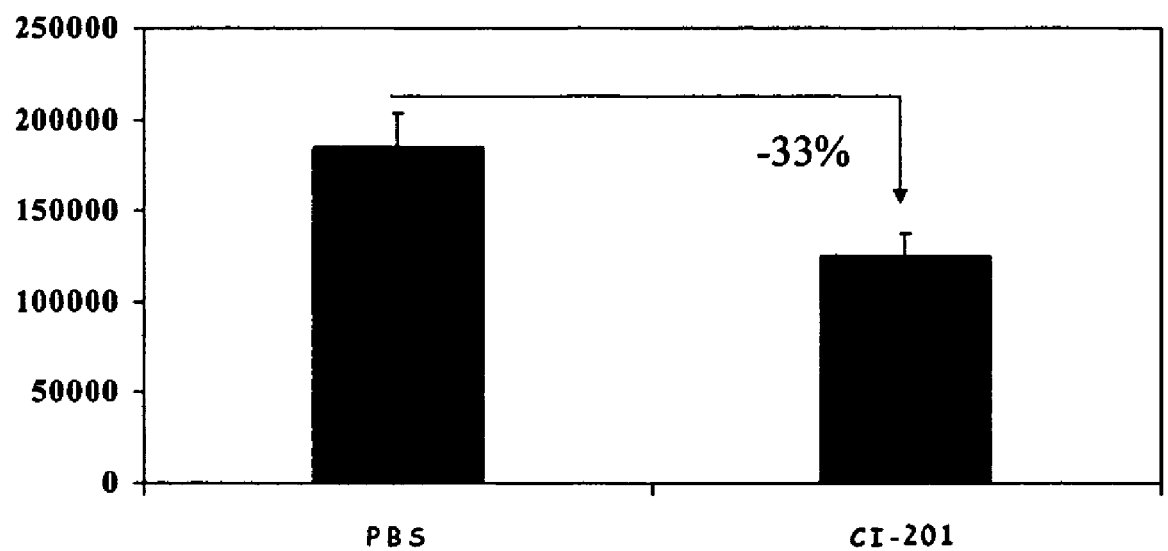

FIG. 7 is a graphic representation demonstrating inhibition of progression of late-stage atherogenesis in apoE-knock out mice by oral tolerance induced with the synthetic oxidized phospholipids D-ALLE, L-ALLE or POVPC. 24.5 week old apo-E knock out mice were fed 1 mg/mouse L-ALLE (L-ALLE) (n=11), D-ALLE (D-ALLE) (n=9) or POVPC (POVPC) (n=10) every other day for 5 days, at 4 week intervals over a 12 week period. Control mice were fed an identical volume (0.2 ml) and regimen of PBS (CONTROL) (n=10). Atherogenesis is expressed as the area of atheromatous lesions in the aortic sinus 12 weeks after the first feeding, as compared to the lesion scores of untreated 24.5 week old mice before feeding (Time 0);

FIG. 8 is a graphic representation demonstrating reduction of triglyceride content of VLDL in apoE-knock out mice induced by feeding synthetic oxidized phospholipids D-ALLE, L-ALLE or POVPC. 24.5 week old apo-E mice were fed 1 mg/mouse L-ALLE (triangle) (n=11), D-ALLE (inverted triangle) (n=9) or POVPC (square) (n=10) every other day for 5 days, at 4 week intervals over a 12 week period. Control mice were fed an identical volume (0.2 ml) and regimen of PBS (circle) (n=10). Triglyceride content (Tg, mg/ml) was measured 9 weeks from t=0, by enzymatic colorimetric method in the VLDL fractions following separation of pooled blood samples on FPLC, as described in the materials and methods section that follows;

FIG. 9 is a graphic representation demonstrating reduction of cholesterol content of VLDL in apoE-knock out mice induced by feeding synthetic oxidized phospholipids D-ALLE, L-ALLE or POVPC. 24.5 week old apo-E mice were fed 1 mg/mouse L-ALLE (triangle) (n=11), D-ALLE (inverted triangle) (n=9) or POVPC (square) (n=10) every other day for 5 days, at 4 week intervals over a 12 week period. Control mice were fed an identical volume (0.2 ml) and regimen of PBS (circle) (n=10). Cholesterol content (Cholesterol, mg/ml) was measured 9 weeks from t=0, by enzymatic colorimetric method in the VLDL fractions following separation of pooled blood samples on FPLC, as described in the materials and methods section that follows;

FIG. 10 presents 2D structural descriptions of 1-Hexadecyl-2-(5'-Carboxy-butyl)-sn-glycero-3-phosphocholine (IC-201, Compound I), 1-Hexadecyl-2-(5',5'-Dimethoxy-pentyloxy)-sn-glycero-3 -phosphocholine (Compound IIa) and 1-Hexadecyl-2-(5',5'-Diethoxy-pentyloxy)-sn-glycero-3-phosphocholine (Compound IIb);

FIG. 11 is a graphic representation demonstrating inhibition of early atherogenesis in apoE-knock out mice by oral tolerance induced by feeding CI-201. 12 week old apo-E mice were fed CI-201: 0.025 mg/mouse (n=14); or 0.2 ml PBS (CONTROL) (n=15) every day for 8 weeks (5 times a week). Atherogenesis is expressed as the area of atheromatous lesions in the aortic sinus. Atherosclerosis is expressed as the area of atheromatous lesion in the aortic sinus 11 weeks after the first feeding; and FIGS. 12a-d present photographs demonstrating the cytokine expression levels in the aorta of mice treated with ALLE, CI-201, its ethyl acetal derivative (Et-acetal), its methyl acetal derivative (Me-acetal), oxLDL or PBS. Particularly, FIGS. 12a and 12b present the elevation of IL-10 expression level in the aorta of mice treated with ALLE, CI-201, Et-acetal, Me-acetal and oxLDL as compared with non-treated mice (PBS) and the reduced IFN-gamma expression levels in aortas from mice treated with ALLE, CI-201, Me-acetal and oxLDL as compared with PBS treated mice, and FIGS. 12c and 12d present the reduced IL-12 expression in mice treated with ALLE, CI-201 and Et-acetal as compared with PBS treated group. 10-12 weeks old ApoE knock out mice were fed 1 mg/mouse/0.2 ml of the tested antigen (ALLE, CI-201, Et-acetal, Me-acetal) or 0.1 mg/mouse/0.2 ml oxLDL or administered with 0.2 ml PBS. Oral administrations took place 5 times every other day and the cytokine expression was evaluated 8 weeks after the last oral administration.

DESCRIPTION OF THE PREFERRED EMBODIMENTS

The present invention is of methods and compositions employing synthetic oxidized phospholipids effective in inducing mucosal tolerance and inhibiting inflammatory processes contributing to atheromatous vascular disease and sequalae.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Experimental and clinical evidence indicates a causative role for oxidized LDL and LDL components in the etiology of the excessive inflammatory response in atherosclerosis. Both cellular and humoral immune reactivity to plaque related oxidized LDL have been demonstrated, suggesting an important anti-oxidized LDL auto-immune component in atherogenesis. Thus, oxidized LDL and components thereof, have been the targets of numerous therapies for prevention and treatment of heart disease, cerebral-vascular disease and peripheral vascular disease.

Although the prior art teaches that oral administration of LDL can result in 30% reduction in atherogenesis, such a protective effect was observed following administration of a crude antigen preparation consisting of centrifuged, filtered and purified human serum LDL which had been subjected to a lengthy oxidation process with $Cu^{++}$. Although significant inhibition of atherogenesis was achieved, presumably via oral tolerance, no identification of specific lipid antigens or immunogenic LDL components was made.

Another obstacle encountered was the inherent instability of the crude oxidized LDL in vivo, due to enzymatic activity and uptake of oxidized LDL by the liver and cellular immune mechanisms. Such an inherent instability is also associated with in vivo applications that utilize other oxidized LDL derivatives, such as POVPC and PGPC (described hereinabove).

In view of the growing need for oxidized LDL derivatives devoid of these inherent instability, and as the presently known studies that relate to atherogenesis involve synthetic oxidized LDL derivatives that typically include esterified phospholipids such as 1,2-O-fatty acyl phosphoglycerides, the present inventors have envisioned that synthetic oxidized LDL derivatives which include etherified phospholipids can serve as stable, novel agents for inducing immune tolerance to oxidized LDL.

While reducing the present invention to practice, the present inventors have synthesized a novel class of well-defined synthetic oxidized LDL derivatives (etherified phospholipids) and have uncovered that administration of such oxidized LDL derivatives can induce immune tolerance to oxidized LDL and thus inhibit atherogenesis, while avoiding the abovementioned limitations.

Hence, according to one aspect of the present invention there is provided a compound having the general formula:

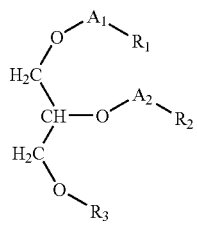

or pharmaceutically acceptable salts thereof, wherein:
(i) $A_1$ and $A_2$ are each independently selected from the group consisting of $CH_2$ and C=O, at least one of $A_1$ and $A_2$ being $CH_2$;
(ii) $R_1$ and $R_2$ are each independently selected from the group consisting of an alkyl chain having 1-27 carbon atoms and

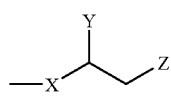

wherein X is an alkyl chain having 1-24 carbon atoms, Y is selected from the group consisting of:

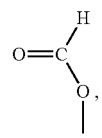

—OH, —H, alkyl, alkoxy halogen, acetoxy and aromatic functional groups; and

Z is selected from the group consisting of:

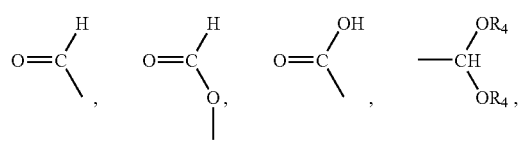

and

—OH, whereas $R_4$ is an alkyl,
at least one of $R_1$ and $R_2$ being

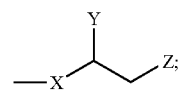

and
(iii) $R_3$ is selected from the group consisting of H, acyl, alkyl, phosphatidyl choline, phosphatidyl ethanolamine, phosphatidyl serine, phosphatidyl cardiolipin and phosphatidyl inisitol.

In one embodiment of the present invention, one of $A_1$ and $A_2$ is $CH_2$ and hence the compound of the present invention is a mono-etherified phospholipid having an O-fatty acyl component. However, in a preferred embodiment of the present invention each of $A_1$ and $A_2$ is $CH_2$ and hence the compound of the present invention is a dietherified phospholipid. Such dietherified phospholipids do not include the inherent instable O-fatty acyl component and are hence characterized by improved in vivo stability, particularly as compared with the presently known synthetic oxidized pholpholipids (e.g., POVPC and PGPC).

As is described in the formula hereinabove, at least one of $R_1$ and $R_2$ is an oxidized alkyl chain. However, since in naturally occuring oxidized LDL derivatives the oxidized alkyl chain is typically located at the second position, and since it has been demonstrated that the biological activity of several phospholipids directly depends on the structure thereof (see the Background section for a detailed discussion), in a preferred embodiment of the present invention $R_1$ is a non-oxidized alkyl chain while $R_2$ is an oxidized alkyl chain.

As is further described in the formula hereinabove, the oxidized alkyl chain include oxidized functional groups such as

(aldehyde),

(carboxylic acid) and

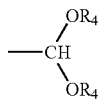

(acetal).

One example of a novel etherified oxidized phospholipid of the present invention is 2,5'-Aldehyde Lecithin Ether (ALLE): 1-hexadecyl-2-(5'-oxo-pentanyl)-sn-glycero-3-phosphocholine (D-ALLE), 3-hexadecyl-2-(5'-oxo-pentanyl)-sn-glycero-1-phosphocholine (L-ALLE)], and the racemic mixture thereof, the synthesis and use of which are further detailed in the Examples section which follows.

However, as aldehydes are known as unstable compounds, which tend to be easily oxidized, preferred examples of novel etherified oxidized phospholipids according to the present invention include the acid derivative 1-Hexadecyl-2-(5'-Carboxy-butyl)-sn-glycero-3-phosphocholine (also referred to hereinafter as IC-201), and its corresponding acetals 1-Hexadecyl-2-(5',5'-Dimethoxy-pentyloxy)-sn-glycero-3-phosphocholine and 1-Hexadecyl-2-(5',5'-Diethoxy-pentyloxy)-sn-glycero-3-phosphocholine (see FIG. 10 for 2-D structural formulas), the synthesis and use of which are also further detailed in the Examples section which follows.

In this respect it should be noted that carboxylic acid derivatives of oxidized etherified phospholipids have been disclosed in CH Pat. No. 642,665. However, CH Pat. No. 642,665 teaches etherified phospholipids in which the carboxylic acid is located at the first position of the phospholipid backbone and hence, as is discussed hereinabove, it is assumed that such compounds would not be as biologically active as the corresponding compounds bearing the carboxylic acid group at the second position of the phospholipid backbone. Studies on the structure-activity relationship with respect to the location of the oxidized alkyl chain in the phospholipid backbone, which are aimed at more clearly demonstrating the superior activity of etherified oxidized phospholipids having an oxidized alkyl chain at the second position of the phospholipid backbone, are currently being conducted by the present inventors.

As is described in the formula hereinabove, $R_3$ is either a phosphatidyl moiety (e.g., phosphatidyl choline, phosphatidyl ethanolamine, etc.) or a non-phosphatidyl moiety (e.g., acyl or alkyl). When $R_3$ is a non-phosphatidyl moiety, the resultant compound is not a phospholipid, rather a diglyceride compound. Such diglyceride compounds retain similar structure characteristics and as such in all probability would posses antigenicity and immune tolerizing activity. Thus, these compounds can also be used in prevention and/or treatment of atherosclerosis related disorders, and employed and applied similarly to the oxidized phospholipid derivatives described herein.

As is described in the Examples section that follows, the compounds of the present invention have been found to induce immune tolerance to oxidized LDL.

Thus, according to another aspect of the present invention there is provided a method of inducing immune tolerance to oxidized LDL in a subject such as a human being. Such immune tolerance can be used in the prevention and/or treatment of disorders associated with plaque formation, including but not limited to atherosclerosis, atherosclerotic cardiovascular disease, cerebrovascular disease, peripheral vascular disease, stenosis, restenosis and in-stent-stenosis. Some non-limiting examples of atherosclerotic cardiovascular disease are myocardial infarction, coronary arterial disease, acute coronary syndromes, congestive heart failure, angina pectoris and myocardial ischemia. Some non-limiting examples of peripheral vascular disease are gangrene, diabetic vasculopathy, ischemic bowel disease, thrombosis, diabetic retinopathy and diabetic nephropathy. Non-limiting examples of cerebrovascular disease are stroke, cerebrovascular inflammation, cerebral hemorrhage and vertebral arterial insufficiency. Stenosis is occlusive disease of the vasculature, commonly caused by atheromatous plaque and enhanced platelet activity, most critically affecting the coronary vasculature. Restenosis is the progressive re-occlusion often following reduction of occlusions in stenotic vasculature. In cases where patency of the vasculature requires the mechanical support of a stent, in-stent-stenosis may occur, re-occluding the treated vessel.

As is further detailed in the Examples section which follows, the method, according to this aspect of the present invention is effected by administering to the subject a therapeutically effective amount of the synthetic etherified oxidized phospholipids of the present invention described hereinabove.

Recently, phospholipids and phospholipid metabolites have been clearly implicated in the pathogenesis, and therefore potential treatment, of additional, non-atherosclerosis-related diseases. Such diseases and syndromes include, for example, oxidative stress of aging (Onorato J M, et al, Annal NY Acad Sci 1998 Nov. 20; 854:277-90), rheumatoid arthritis (RA) (Paimela L, et al. Ann Rheum Dis 1996 August; 55(8):558-9), juvenile rheumatoid arthritis (Savolainen A, et al, 1995; 24(4):209-11), inflammatory bowel disease (IBD) (Sawai T, et al, Pediatr Surg Int 2001 May; 17(4):269-74) and renal cancer (Noguchi S, et al, Biochem Biophys Res Commun 1992 Jan. 31; 182(2):544-50). Thus, the compounds of the present invention can also be used in a method for prevention and/or treatment of non-atherosclerosis related diseases such as inflammatory disorders, immune mediated diseases, autoimmune diseases and proliferative disorders. Non-limiting examples of such disorders and diseases include aging, RA, juvenile RA, IBD and cancer, as is described hereinabove.

While the etherified oxidized phospholipids of the present invention can be synthesized using modifications of prior art approaches, while reducing the present invention to practice, the present inventors have uncovered a novel method for synthesizing such compounds, which can also be utilized for synthesizing other classes of oxidized phospholipids (e.g., esterified oxidized phospholipids).

Thus, according to another aspect of the present invention there is provided a method of synthesizing an oxidized phospholipid. The method is effected by first providing a phospholipid backbone including two fatty acid side chains, at least one of the fatty acid side chains being a mono-unsaturated fatty acid (preferably a $C_{2-15}$ fatty acid), followed by oxidizing the unsaturated bond of the mono-unsaturated fatty acid, thereby generating the oxidized phospholipid.

The oxidation of the unsaturated bond can be performed using known oxidizing agents such as, for example, potassium meta periodate.

Examples of phospholipid backbones suitable for synthesis of, for example, an esterified oxidized phospholipid according to the teachings of the present invention include, but are not limited to lecithin, which includes two O-fatty acyl side chains, and lysolecithin which includes a single O-fatty acyl side chain and as such must undergo an additional synthesis step of adding an additional fatty acid side chain prior to oxidation.

The novel synthesis method of the present invention can be used, for example, for synthesizing the esterified phospholipid POVPC, which, as is detailed in the Background section hereinabove, is known to be associated with atherogenesis. When utilized to synthesize POVPC, the phospholipid backbone includes 5-hexenoic acid as the mono-unsaturated fatty acid side chain.

The novel synthesis approach of the present invention provides several advantages over prior art synthesis approaches. In this synthetic method, a defined mono unsaturated acid of desired length and structure is reacted with a molecule having lysolecithin backbone to give monounsaturated phospholipids, which is then oxidized at the desired unsaturated double bond.

The advantages of such a novel approach is in its specificity and simplicity. Oxidizing mono-unsaturated phospholipids having lecithin backbone results in a single, desired specific product and therefore commercial product work up and purification is made much more efficient.

Such a reaction provides specific, desired oxidized phospholipids, traversing the need to perform complicated separations and purification.

Furthermore, using this method it is possible to design and synthesize oxidized phospholipids by oxidation of mono-unsaturated phospholipids with a double bond at the end of the chain, enabling the use of substantially short unsaturated acid chains in the synthetic process. Such mono-unsaturated short acid chains are relatively inexpensive, and thus reducing the costs associated with synthesis. As such, the synthesis method of the present invention could therefore be conveniently adapted for large-scale manufacturing processes.

A detailed description of synthesis of etherified and esterified oxidized phospholipids according to the teachings of the present invention is provided in the Examples section which follows.

The immune tolerance inducing compounds described herein can be utilized in the therapeutic applications described hereinabove, by being administered per se, or in a pharmaceutical composition where it is mixed with suitable carriers or excipients.

Thus, according to another aspect of the present invention, there are provided pharmaceutical compositions for prevention and/or treatment of atherosclerosis, cardiovascular disorders, cerebrovascular disorders, peripheral vascular disease, stenosis, restenosis and/or in-stent-stenosis in a subject in need thereof. The pharmaceutical compositions according to this aspect of the present invention comprise, as an active ingredient, a therapeutically effective amount of the etherified oxidized phospholipid of the present invention or any other synthetic oxidized LDL derivative and a pharmaceutically acceptable carrier.

The pharmaceutical compositions of the present invention can further be used for prevention and/to treatment of inflammatory disorders, immune mediated diseases, autoimmune diseases and proliferative disorders such as, but not limited to, aging, RA, juvenile RA, IBD and cancer.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the compounds (e.g., ALLE and CI-201) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

In a preferred embodiment of the present invention, the pharmaceutical compositions are designed for inducing tolerance to Ox LDL via mucosal administration.

Further preferably, the pharmaceutical compositions of the present invention are designed for nasal, oral or intraperitoneal administration, as is detailed hereinafter.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of a disorder (e.g., atherosclerosis) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress angiogenesis (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack.

The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The present invention illustrates for the first time that synthetic derivatives of oxidized phospholipids, etherified oxidized phospholipids in particular, can be used to prevent and treat atherosclerosis in a subject, while being devoid of limitations inherent to treatments utilizing biologically derived forms of oxidized LDL or other classes of synthetic derivatives of oxidized LDL.

The present invention also provides a novel approach for synthesizing oxidized phopholipids. The present invention also provides novel oxidized phospholipid ethers, utilizable for treatment of atherosclerosis and related disorders, as well as other inflammatory and immune related disorders and diseases.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include biochemical and immunological techniques. Such techniques are thoroughly explained in the literature. See, for example, "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; and "Methods in Enzymology" Vol. 1-317, Academic Press; Marshak et al., all of which are incorporated by reference as if fully set forth herein. Other general references are provided throughout this document. The procedures therein are believed to be well known in the art and are provided for the convenience of the reader. All the information contained therein is incorporated herein by reference.

Materials and General Methods

Animals:

Apo-E knock out mice used in our experiments are from the atherosclerosis prone strain C57BL/6J-Apoe$^{tm1unc}$. Mice homozygous for the Apoe$^{tm1unc}$ mutations show a marked increase in total plasma cholesterol levels which is unaffected by age or sex. Fatty streaks in the proximal aorta are found at 3 months of age. The lesions increase with age and progress to lesions with less lipid but more elongated cells, typical of a more advanced stage of pre-atherosclerotic lesion.

Strain Development: The Apoe$^{tm1unc}$ mutant strain was developed in the laboratory of Dr. Nobuyo Maeda at University of North Carolina at Chapel Hill. The 129-derived E14Tg2a ES cell line was used. The plasmid used is designated as pNMC109 and the founder line is T-89. The C57BL/6J strain was produced by backcrossing the Apoe$^{tm1unc}$ mutation 10 times to C57BL/6J mice [11,12].

The mice were maintained at the Sheba Hospital Animal Facility (Tel-Hashomer, Israel) on a 12-hour light/dark cycle, at 22-24° C. and fed a normal fat diet of laboratory chow (Purina Rodent Laboratory Chow No. 5001) containing 0.027% cholesterol, approximately 4.5% total fat, and water, ad libitum.

Immunization:

I. Intraperitoneal immunization with ALLE: The phospholipid ether analog (ALLE D+L) was coupled to purified protein derivative from tuberculin (PPD). The stock solution of ALLE (D+L) was dissolved in ethanol (99 mg/ml). 5 mg ALLE (D+L), (50.5 µl from stock solution) was diluted to 5 mg/ml with 0.25M phosphate buffer, pH 7.2, by stirring on ice. 1.5 mg of D- and L-ALLE in 300 µl of phosphate buffer were added to 0.6 mg PPD dissolved in 300 µl of phosphate buffer. 1-Ethyl-3-(3-dimethylaminopropyl)-carbodiimid-HCl (5 mg; Sigma, St. Louis, Mo.) dissolved in 50 µl of water was added by stirring at 4° for 20 min. The remaining active sites were blocked with 100 µl of 1M glycine. Coupled compounds were dialyzed against phosphate-buffered saline (PBS), adjusted to 3 ml with PBS and stored at 4° C. Immunization with 0.3 ml (150 µg) antigen per mouse was performed intraperitoneally 4 times every 2 weeks.

II. Subcutaneous immunization with Human oxidized LDL: Human oxidized LDL was prepared from human plasma pool (d-1.019 to 1.063 gram/ml by ultracentrifugation) and was Cu-oxidized overnight (by adding 15 µl 1 mM $CuSO_4$ to each ml of LDL previously diluted to 1 mg/ml concentration). The oxidized LDL was dialyzed against PBS and filtrated. For immunization, oxidized LDL was dissolved in PBS and mixed with equal volumes of Freund's incomplete adjuvant. Immunizations were performed by single subcutaneous injection of 50 µg antigen/mouse in 0.2 ml volume. One to three days following the last oral administration the mice received one immunization, and were sacrificed 7-10 days post immunization.

Cholesterol Level Determination: At the completion of the experiment, 1-1.5 ml of blood was obtained by cardiac puncture, 1000 U/ml heparin was added to each sample and total plasma cholesterol levels were determined using an automated enzymatic technique (Boehringer Mannheim, Germany).

FPLC Analysis: Fast Protein Liquid Chromatography analysis of cholesterol and lipid content of lipoproteins was performed using Superose 6 HR 10/30 column (Amersham Pharmacia Biotech, Inc, Peapack, N.J.) on a FPLC system (Pharmacia LKB. FRAC-200, Pharmacia, Peapack, N.J.). A minimum sample volume of 300 µl (blood pooled from 3 mice was diluted 1:2 and filtered before loading) was required in the sampling vial for the automatic sampler to completely fill the 200 μl sample loop. Fractions 10-40 were collected, each fraction contained 0.5 ml. A 250 μl sample from each fraction was mixed with freshly prepared cholesterol reagent or triglyceride reagent respectively, incubated for 5 minutes at 37° C. and assayed spectrophotometrically at 500 nm.

Assessment of Atherosclerosis: Quantification of atherosclerotic fatty streak lesions was done by calculating the lesion size in the aortic sinus as previously described [16] and by calculating the lesion size in the aorta. Briefly, after perfusion with saline Tris EDTA, the heart and the aorta were removed from the animals and the peripheral fat cleaned carefully. The upper section of the heart was embedded in OCT medium (10.24% w/w polyvinyl alcohol; 4.26% w/w polyethylene glycol; 85.50% w/w nonreactive ingredients) and frozen. Every other section (10 μm thick) throughout the aortic sinus (400 μm) was taken for analysis. The distal portion of the aortic sinus was recognized by the three valve cusps that are the junctions of the aorta to the heart. Sections were evaluated for fatty streak lesions after staining with oil-red O. Lesion areas per section were scored on a grid [17] by an observer counting unidentified, numbered specimens. The aorta was dissected from the heart and surrounding adventitious tissue was removed. Fixation of the aorta and Sudan staining of the vessels were performed as previously described [21].

Proliferation assays: Mice were fed with ALLE, POVPC or PBS as described for assessment of atherosclerosis, and then immunized one day following the last feeding with oxidized LDL prepared from purified human LDL as described above.

Proliferation was assayed eight days after immunization with the oxidized LDL as follows: Spleens or lymph nodes were prepared by meshing the tissues on 100 mesh screens. (Lymph nodes where immunization was performed, and spleens where no immunization performed). Red blood cells were lysed with cold sterile double distilled water (6 ml) for 30 seconds and 2 ml of NaCl 3.5% were added. Incomplete medium was added (10 ml), cells were centrifuge for 7 minutes at 1,700 rpm, resuspended in RPMI medium and counted in a haemocytometer at 1:20 dilution (10 μl cells+190 μl Trypan Blue). Proliferation was measured by the incorporation of [$^3$H]-Thymidine into DNA in triplicate samples of 100 μl of the packed cells ($2.5 \times 10^6$ cells/ml) in a 96 well microtiter plate. Triplicate samples of oxidized LDL (0-10 μg/ml, 100 μl/well) were added, cells incubated for 72 hours (37° C., 5% $CO_2$ and about 98% humidity) and 10 μl $^3$[H]-Thymidine (0.5 μCi/well) were added. After an additional day of incubation the cells were harvested and transferred to glass fiber filters using a cell harvester (Brandel) and counted using β-counter (Lumitron). For assay of cytokines the supernatant was collected without adding $^3$[H]-Thymidine and assayed by ELISA.

A separate group of mice were fed with ALLE or PBS and immunized with oxidized LDL as described above, one day following the last fed dose. Draining inguinal lymph nodes (taken 8 days after immunization) were collected from 3 mice from each of the groups, for the proliferation studies. $1 \times 10^6$ cells per ml were incubated in triplicates for 72 hours in 0.2 ml of culture medium in microtiter wells in the presence 10 μg/ml oxidized LDL. Proliferation was measured by the incorporation of [$^3$H]-thymidine into DNA during the final 12 hours of incubation. The results are expressed as the stimulation index (S.I.): the ratio of the mean radioactivity (cpm) of the antigen to the mean background (cpm) obtained in the absence of the antigen. Standard deviation was always <10% of the mean cpm.

RT-PCR analysis: Aortas were removed out of treated and untreated mice (in a sterile manner) and freezed in liquid nitrogen. The aorta were mashed on screen cup and the RNA production was performed using Rneasy kit (QIAGEN). RNA samples were examined in spectrophotometer and normalized relative to β-actin. Reverse transcription of RNA to cDNA and PCR with primers was performed with "Titan one tube RT-PCR kit" (ROCHE). Results were detected on 1% agarose gel and were documented on film.

Statistical Analysis: A one way ANOVA test was used to compare independent values. $p<0.05$ was accepted as statistically significant.

Example I

Synthesis of the Tolerizing/immunizing Antigens 2,5'-Aldehyde Lecithin Ether (ALLE) and POVPC

ALLE

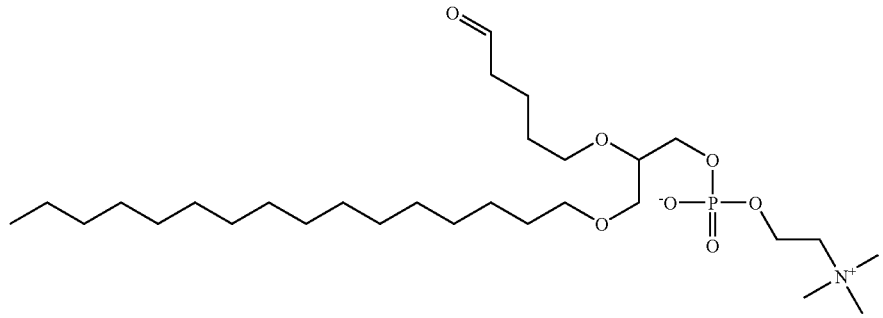

1-hexadecyl-2-(5'-oxo-pentanyl)-sn-glycero-3-phosphocholine

POVPC

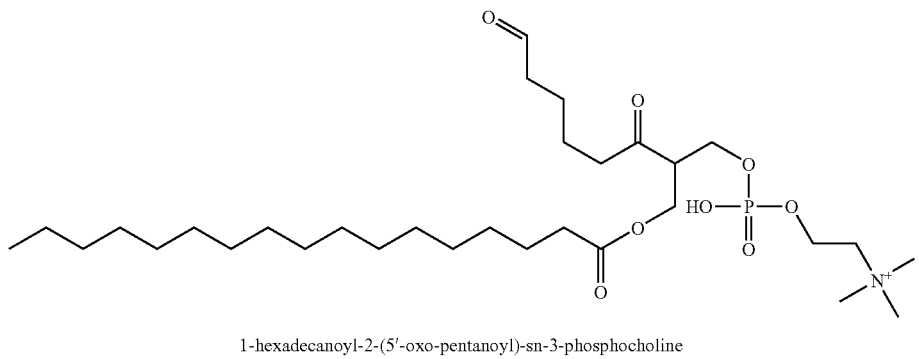

1-hexadecanoyl-2-(5'-oxo-pentanoyl)-sn-3-phosphocholine

Synthesis of 2,5'-Aldehyde Lechitin Ether (ALLE)

2,5'-Aldehyde Lecithin Ether (ALLE) was synthesized according to a modification of general methods for synthesis of ether analogs of lecithins communicated by Eibl H., et al. Ann. Chem. 709:226-230, (1967), W. J. Baumann and H. K. Mangold, J. Org. Chem. 31, 498 (1996), E. Baer and Buchnea JBC. 230, 447 (1958), Halperin G et al Methods in Enzymology 129, 838-846 (1986). The following protocol refers to compounds and processes depicted in 2-D form in FIG. 1.

Hexadecyl-glycerol ether: D-Acetone glycerol (4 grams) for synthesis of L-ALLE or L-Acetone glycerol for synthesis of D-ALLE, powdered potassium hydroxide (approximately 10 grams) and hexadecyl bromide (9.3 grams) in benzene (100 ml) were stirred and refluxed for 5 hours, while removing the water formed by azeotropic distillation (compare W. J. Baumann and H. K. Mangold, J. Org. Chem. 29: 3055, 1964 and F. Paltauf, Monatsh. 99:1277, 1968). The volume of the solvent was gradually reduced to about 20 ml, and the resulting mixture was cooled to room temperature and dissolved in ether (100 ml). The resulting solution was washed with water (2×50 ml), and the solvent was removed under reduced pressure. A 100 ml mixture of 90:10:5 methanol:water:concentrated hydrochloric acid was added to the residue and the mixture was refluxed for 10 minutes. The product was extracted with ether (200 ml) and was washed consecutively with water (50 ml), 10% sodium hydroxide (20 ml) and again with water (volumes of 20 ml) until neutral. The solvent was removed under reduced pressure and the product (8.8 grams) was crystallized from hexane to give 7.4 grams of pure 1-hexadecyl-glyceryl ether (compound I, FIG. 1) for synthesis of D-ALLE or 3-hexadecyl-glyceryl ether for synthesis of L-ALLE.

5-Hexenyl-methane sulfonate: A mixture of 5-hexene-1-ol (12 ml) and dry pyridine (25 ml) was cooled to between −4° C. and −10° C. in an ice-salt bath. Methanesulfonyl chloride (10 ml) was added dropwise during a period of 60 minutes, and the mixture was kept at 4° C. for 48 hours. Ice (20 grams) was added, the mixture was allowed to stand for 30 minutes, and the product was extracted with ether (200 ml). The organic phase was washed with water (20 ml), 10% hydrochloric acid, 10% sodium bicarbonate (20 ml) and again with water (20 ml). The solvent was evaporated and the crude product was chromatographed on silica gel 60 (100 grams) using a mixture of 80:20 $CHCl_3$:EtOAc as eluent, to give 14 grams of 5-hexenyl-methane sulfonate.

1-Hexadecyloxy-3-trityloxy-2-propanol (for D-ALLE) or 3-Hexadecyloxy-1-trityloxy-2-propanol (for L-ALLE) (compound II): 1-Hexadecyloxy-glycerol (for D-ALLE) or 3-Hexadecyloxy-glycerol (for L-ALLE) (7.9 grams), triphenylchloromethane (8.4 grams) and dry pyridine (40 ml) were heated at 100° C. for 12 hours. After cooling, 300 ml of ether and 150 ml of ice-cold water were added, and the reaction mixture was transferred to a separatory funnel. The organic phase was washed consecutively with 50 ml of ice water, 1% potassium carbonate solution (until basic) and 50 ml of water, then dried over anhydrous sodium sulfate. The solvent was evaporated, the residue was dissolved in 150 ml of warm petroleum ether and the resulting solution was cooled at 4° C. over night. After filtration of the precipitate, the filtrate was evaporated and the residue was recrystallized from 20 ml of ethyl acetate at −30° C., yielding 8.2 grams of 1-Hexadecyloxy-3-trityloxy-2-propanol (for D-ALLE) or 3-hexadecyloxy-1 -trityloxy-2-propanol (for L-ALLE) (compound II, FIG. 1), melting point 49° C.

1-Hexadecyl-2-(5'-hexenyl)-glyceryl ether (for D-ALLE) or 3-hexadecyl-2-(5'-hexenyl)-glyceryl ether (for L-ALLE) (compound IV): 1-Hexadecyloxy-3-trityloxy-2-propanol (for D-ALLE) or 3-Hexadecyloxy-1-trityloxy-2-propanol (for L-ALLE) (compound II, FIG. 1) (5.5 grams) was etherified with 5-hexenyl-methanesulfonate, using powdered potassium hydroxide in benzene solution as described above. The crude product 1-Hexadecyloxy-2-(5'-hexenyloxy)-sn-3-trityloxy-propane (for D-ALLE) or 3-Hexadecyloxy-2-(5'-hexenyloxy)-sn-3-trityloxy-propane (for L-ALLE) (compound III, FIG. 1) was dissolved in 100 ml of 90:10:5 methanol:water:concentrated hydrochloric acid and the mixture was refluxed for 6 hours. The product was extracted with ether, washed with water and the solvent was removed. The residue was dissolved in petroleum ether (100 ml) and was kept in 4° C. for overnight, causing most of the triphenyl carbinol to be deposited. After filtration and removal of the solvent from the filtrate the crude product was chromatographed on silica gel 60 (40 grams), using a mixture of 1:1 chloroform:petroleum ether as eluent, to give 1.8 grams of pure 1-hexadecyl-2-(5'-hexenyl)-glyceryl ether (for D-ALLE) or 3-hexadecyl-2-(5'-hexenyl)-glyceryl ether (for L-ALLE) (compound IV, FIG. 1).

1-Hexadecyl-2-(5'-hexenyl)-sn-glycero-3-phosphocholine (for D-ALLE) or 3-Hexadecyl-2-(5'-hexenyl)-sn-glycero-1-phosphocholine (for L-ALLE) (compound V): The following procedure is a modification of the method communicated by Eibl H., et al. Ann. Chem. 709:226-230, 1967.

A solution of 1-hexadecyl-2-hexenyl-glyceryl ether (for D-ALLE) or 3-hexadecyl-2-hexenyl-glyceryl ether (for L-ALLE) (compound IV, FIG. 1) (2 grams) in dry chloroform (15 ml) was added dropwise into a stirred, cooled solution (−4° C. to −10° C.) of dry triethylamine (3 ml) and 2-bromoethyl dichlorophosphate (1.25 ml, prepared as described hereinbelow) in dry chloroform (15 ml), during a period of 1 hour. The mixture was kept at room temperature for 6 hours and then heated to 40° C. for 12 hours. The resulting dark brown solution was cooled to 0° C. and 0.1M potassium chloride (15 ml) was added. The mixture was allowed to reach room temperature and was stirred for 60 minutes. Methanol (25 ml) and chloroform (50 ml) were added and the organic phase was washed with 0.1M hydrochloric acid (20 ml) and water (20 ml). The solvent was evaporated and the crude product was dissolved in methanol (15 ml), the solution was transferred to a culture tube and was cooled in an ice-salt bath. Cold trimethylamine (3 ml, −20° C.) was added and the tube was sealed. The mixture was heated to 55° C. for 12 hours, cooled to room temperature and the solvent evaporated using a stream of nitrogen. The residue was extracted with a mixture of 2:1 chloroform:methanol (25 ml) and washed with 1M potassium carbonate (10 ml) and water (2×10 ml). The solvent was removed under educed pressure and the crude products were chromatographed on silica gel 60 (20 grams), using a mixture of 60:40 chloroform:methanol, to give 1.5 grams of 1-hexadecyl-2-(5'-hexenyl)-sn-glycero-3-phosphocholine (for D-ALLE) or 3-hexadecyl-2-(5'-hexenyl)-sn-glycero-1-phosphocholine (for L-ALLE) (compound V, FIG. 1). The structure of compound V was confirmed by NMR and mass spectrometry.

1-Hexadecyl-2-(5'-oxo-pentanyl)-sn-glycero-3-phosphocholine (for D-ALLE) or 3-Hexadecyl-2-(5'-oxo-pentanyl)-sn-glycero-1-phosphocholine (for L-ALLE) (compound VI)

A solution of Compound V (0.5 gram) in formic acid (15 ml) and 30% hydrogen peroxide (3.5 ml) was stirred at room temperature over night. The reaction mixture was diluted with water (50 ml), and extracted with a mixture of 2:1 chloroform:methanol (5×50 ml). The solvent was evaporated under reduced pressure and the residue was mixed with methanol (10 ml) and water (4 ml), then stirred at room temperature for 60 minutes. 80% phosphoric acid (2 ml) and potassium meta periodate (0.8 gram) were then added. The mixture was kept at room temperature overnight, diluted with water (50 ml) and extracted with 2:1 chloroform:methanol (50 ml). The organic phase was washed with 10% sodium bisulfite (10 ml) and water (10 ml). The solvent was removed under reduced pressure and the crude product was chromatographed on silica gel 60 (10 grams), using a mixture of 1:1 chloroform:methanol as eluent, to give 249 mg of 1-hexadecyl-2-(5'-oxo-pentanyl)-sn-glycero-3-phosphocholine (for D-ALLE) or 3-hexadecyl-2-(5'-oxo-pentanyl)-sn-glycero-1-phosphocholine (for L-ALLE) (compound VI, FIG. 1), exhibiting an $R_f$ of 0.15 (TLC system, 60:40:8 chloroform:methanol:water) and a positive reaction with dinitrophenylhydrazine. The chemical structure of Compound VI was confirmed by NMR and mass spectrometry.

In an alternative process, the ethylenic group was converted to an aldehyde group by ozonization and catalytic hydrogenation with palladium calcium carbonate.

Preparation of 2-bromoethyl dichlorophosphate: 2-Bromoethyl dichlorophosphate was prepared by dropwise addition of freshly distilled 2-bromoethanol (0.5M, prepared as described in Gilnan Org. Synth. 12:117, 1926) to an ice-cooled solution of freshly distilled phosphorous oxychloride (0.5M) in dry chloroform, during a one hour period, followed by 5 hours reflux and vacuum distillation (bp 66-68° C. at 0.4-0.5 mm Hg). The reagent was stored (−20° C.) under nitrogen in small sealed ampoules prior to use (Hansen W. H et al. Lipids 17(6):453-459, 1982).

Synthesis of 1-Hexadecyl-2-(5'-carboxy-butyl)-sn-glycero-3-phosphocholine (CI-201)

1-Hexadecyl-2-(5'-oxo-pentanyl)-sn-glycero-3-phosphocholine (Compound VI, prepared as described above), 0.55 grams (0.001 mol), was dissolved in t-BuOH (30 ml). A solution of NaClO$_2$ (0.9 gram, 0.01 mol) and NaH$_2$PO$_4$ (0.96 gram, 0.07 mol) in 25 ml water was added dropwise during a period of 30 minutes and the mixture was stirred at room temperature for 3 hours. The reaction mixture was acidified to pH=3 with concentrated hydrochloric acid and extracted with a mixture of 2:1 chloroform:methanol. The organic phase was separated and the solvent was evaporated. The residue was purified by chromatography over silica gel using a mixture of chloroform:methanol:water (70:27:3), to give 1-hexadecyl-2-(5'-carboxy-butyl)-sn-glycero-3-phosphocholine (0.42 gram, 72% yield). NMR and mass spectrometry confirmed the chemical structure (Compound I, FIG. 10).

Synthesis of 1-Hexadecyl-2-(5',5'-dimethoxy-pentyloxy)-sn-glycero-3-phosphocholine 1-Hexadecyl-2-(5'-hexenyl)-sn-glycero-3-phosphocholine (compound V, prepared as described above), 0.50 gram (0.89 mmol), was dissolved in formic acid (15 ml) and hydrogen peroxide 30% (3.5 ml) was added. The reaction mixture was stirred overnight at room temperature. After addition of water (50 ml) the product was extracted with a mixture of 2:1 chloroform:methanol (2×50 ml). The organic phase was washed with aqueous 10% sodium bicarbonate (10 ml) and water (10 ml) and the solvent was removed under reduced pressure. The residue (0.4 gram) was dissolved in methanol (10 ml), aqueous 10% sodium hydroxide (4 ml) was then added and the reaction mixture was stirred at room temperature for 1 hour. 80% Phosphoric acid (2 ml) and potassium meta periodate (0.8 gram) were thereafter added and stirring was continued for over night. A mixture of 2:1 chloroform:methanol (50 ml) was then added and the organic phase was washed with aqueous 10% sodium bisulfite (10 ml) and water (10 ml), and the solvent was removed under vacuum. The residue (0.3 gram) was purified by chromatography over silica gel (10 grams) using a mixture of chloroform:methanol (60:40 to 40:60) as graduated eluent, to give 1-hexadecyl-2-(5',5'-dimethoxy-pentyloxy)-sn-glycero-3-phosphocholine (0.25 gram, 46% yield). NMR and mass spectrometry confirmed the chemical structure (Compound IIa, FIG. 10).

Synthesis of 1-Hexadecyl-2-(5',5'-diethoxypentyloxy)-sn-glycero-3-phosphocholine Crude 1-Hexadecyl-2-(5'-hexenyl)-sn-glycero-3-phosphocholine (compound V, prepared as described above), 50 mg (0.088 mmol), was dissolved in ethanol (10 ml), under a nitrogen atmosphere. Triethyl orthoformate (0.053 ml, 0.0476 gram, 0.32 mmol) and 3 drops of conc. sulfuric acid were added and the reaction mixture was stirred overnight at room temperature. Dichloromethane (75 ml) was then added and the reaction mixture was transferred to a separatory funnel, washed successively with water (75 ml), aqueous 2.5% sodium bicarbonate solution (75 ml) and water (75 ml), and was dried over anhydrous sodium sulfate. After filtration, the solvent was removed under vacuum, to give 50 mg of crude 1-hexadecyl-2-(5',5'-diethoxypentyloxy)-sn-glycero-3-phosphocholine. The structure was confirmed by CMR and MS spectroscopy (Compound IIb, FIG. 10).

Synthesis of 1-Hexadecanoyl-2-(5'-oxo-pentanoyl)-sn-3-glycerophosphocholine(POVPC)

Figure 2:
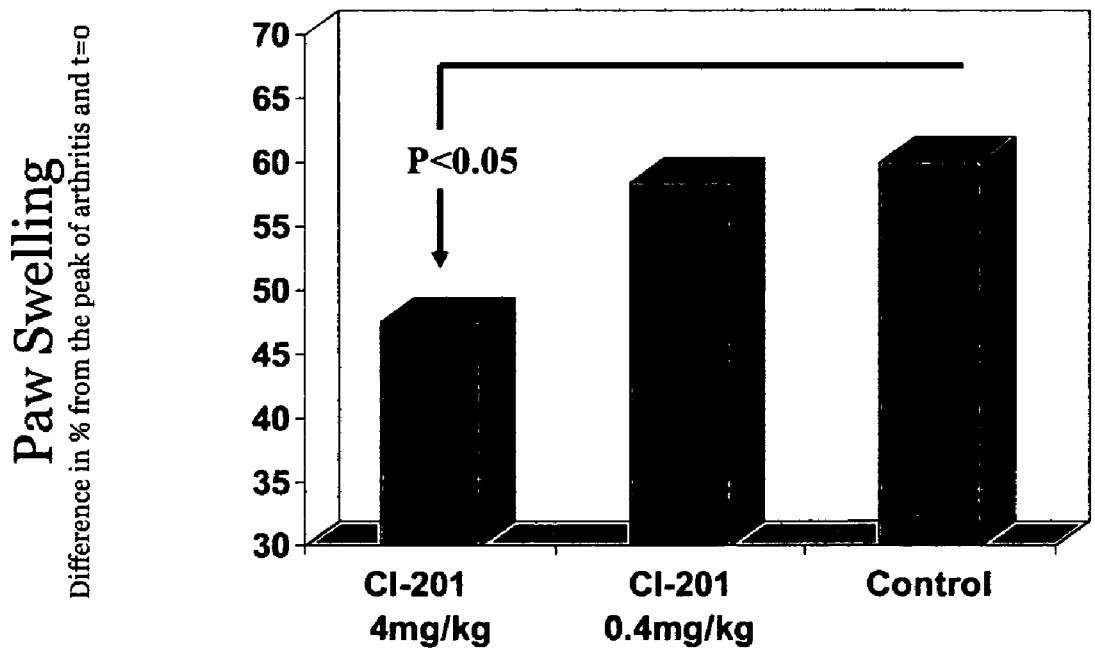
FIG. 2 is a flow chart depicting the synthesis of POVPC according to the present invention.

A mixture of 1-hexadecanoyl-sn-3-glycerophosphocholine (compound I, FIG. 2), L-α-palmitoyl-lysophosphatidylcholine (3 grams), 5-hexenoic acid (1.2 ml), 1,3-dicyclohexylcarbodiamide (DCC, 4.05 grams) and N,N-dimethylaminopyridine (DMP, 1.6 grams) in dichloromethane (100 ml, freshly distilled from phosphorus pentoxide) was thoroughly stirred for 4 days at room temperature. The mixture was then chromatographed on silica gel 60 (40 grams) and the product, 1-hexadecanoyl-2-(5'-hexenoyl)-sn-3-glycerophosphocholine (2.8 grams, compound II, FIG. 2) was eluted with a mixture of 25:75 chloroform:methanol. The eluent was dissolved in 30% hydrogen peroxide:formic acid (4:15) and the solution was stirred overnight at room temperature. Water (50 ml) were added, the product was extracted with 2:1 chloroform:methanol (100 ml) and the organic phase was washed with water. The solvent was evaporated under reduced pressure, the residue was dissolved in methanol (15 ml) and 10% ammonia solution (5 ml) and the solution was stirred at room temperature for 6 hours. The crude 1-hexadecanoyl-2-(5',6'-dihydroxy)-hexanoyl-sn-3-glycerophosphocholine (compound III, FIG. 2) (structure confirmed by NMR and mass spectrometry) was further reacted without purification. 80% phosphoric acid (3 ml) and sodium meta periodate (1 gram) were added to the solution and the mixture was stirred at room temperature for overnight, and was thereafter extracted with a mixture of 2:1 chloroform:methanol. The product was purified by chromatography on silica gel 60 (20 grams), using a mixture of 25:75 chloroform:methanol as eluent. 850 mg of 1-hexadecanoyl-2-(5'-oxopentanoyl)-sn-3-glycerophosphocholine (POVPC, compound IV, FIG. 2) were obtained, exhibiting chromatographic mobility of lecithin on TLC, and positive dinitrophenyl hydrazine reaction. The structure was assessed by NMR and mass spectrometry.

Alternatively: the ethylenic group was converted to an aldehyde by ozonization and catalytic hydrogenation with palladium calcium carbonate.

Example II

Immunization Against L-ALLE+D-ALLE Specifically Inhibits Atherogenesis in Genetically Disposed (ApoE-knock Out) Mice The present inventors have demonstrated that immunization with the stable, etherified synthetic LDL component ALLE can reduce the extent of atherosclerotic plaque formation in susceptible mice. 19 female 5-7 weeks old Apo E/C 57 mice were divided into 3 groups. In group A (n=6) the mice were immunized intraperitoneally, as described in Materials and Methods section above, with 150 µg/mouse L-ALLE+D-ALLE once every 2 weeks (0.3 ml/mouse) X4. In group B (n=6) the mice were immunized with tuberculin toxin Purified Protein Derivative (PPD) once every 2 weeks (0.3 ml/mouse). In group C (n=7) the mice received no immunization. Mice from all three groups were bled prior to immunization (Time 0), and at one week after the second immunization for determination of anti-ox LDL antibodies, anti-ALLE antibodies and lipid profile. Atherosclerosis assessment was performed as described above, 4.5 weeks post $4^{th}$ immunization. The mice from all groups were weighed at 2 week intervals throughout the experiment. All mice were fed normal chow-diet containing 4.5% fat by weight (0.02% cholesterol) and water ad libitum.

TABLE I

Immunization of apoE knock out mice with ALLE inhibits atherogenesis

| Groups | | 150 µg/Mouse L-ALLE + D-ALLE immunization N = 6 | PPD N = 5 | Control without immunization N = 7 | Statistics |
|---|---|---|---|---|---|
| Time 0 | Weight | 17.3 ± 0.5 | 17.3 ± 0.7 | 17.8 ± 0.4 | P = 0.780 |
| | Chol | 435 ± 47 | 436 ± 49 | 413 ± 44 | P = 0.919 |
| | TG | 118 ± 9 | 112 ± 10 | 120 ± 14 | P = 0.865 |
| End | Weight | 20.5 ± 0.5 | 21.6 ± 0.2 | 20.3 ± 0.5 | P = 0.123 |
| | Chol | 299 ± 18 | 294 ± 15 | 3044 ± 22 | P = 0.937 |
| | TG | 57 ± 3 | 53 ± 4 | 66 ± 4 | P = 0.075 |
| | Lesion size (µm$^2$) | 101000 ± 8276 | 179500 ± 13449 | 210833 ± 26714 | P = 0.005 |
| | TGF-β pmol/ml | 12032 ± 2308 | 13963 ± 944 | 12825 ± 2340 | P = 0.831 |

Figure 3:
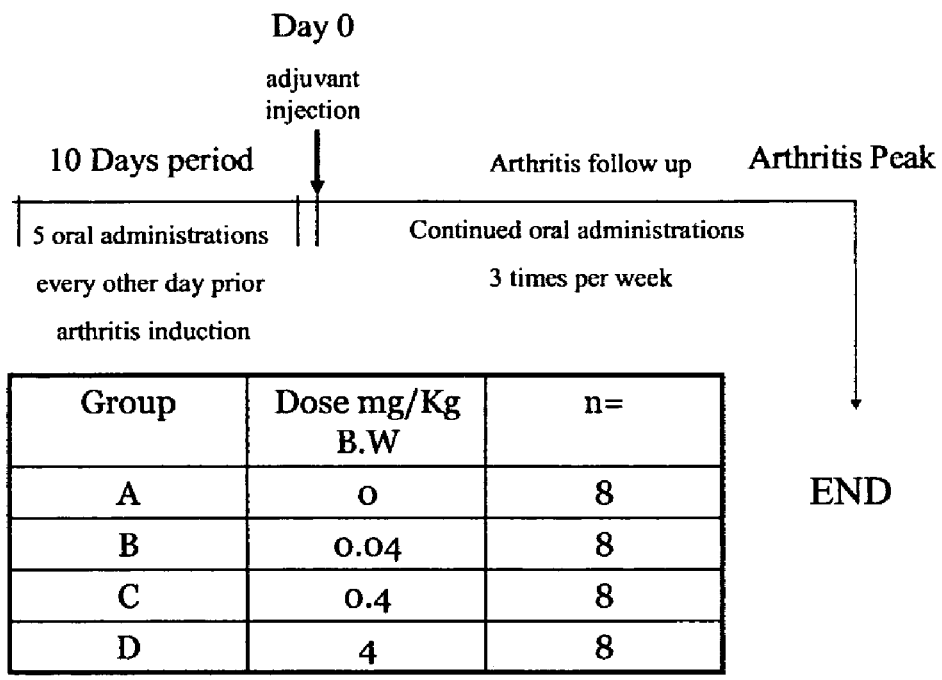
FIG. 3 is a graphic representation demonstrating inhibition of early atherogenesis in apoE-deficient mice by intra peritoneal immunization with mixed D- and L-isomers of ALLE. 5-7 week old apo-E knock out mice were immunized with 150 µg/mouse mixed D- or L-isomers of ALLE coupled to purified tuberculin protein derivative (ALLE L+D) (n=6), purified tuberculin protein derivative alone (PPD) (n=5) or unimmunized (CONTROL) (n=7). Atherogenesis is expressed as the area of atheromatous lesions in the aortic sinus 4.5 weeks following the 4$^{th}$ immunization.

As can be seen in FIG. 3, the results depicted in Table I demonstrate the significant reduction in atheromatous lesions measured in the heart tissues of the ALLE immunized mice, compared to both PPD and unimmunized control mice. No significant effect is apparent on other parameters measured, such as weight gain, triglyceride or cholesterol blood levels, or immune competence, as measured by the levels of the immunosuppressive cytokine TGF-β. Thus, immunization with the synthetic oxidized LDL component ALLE (a mixture of racemic forms D- and L-) confers significant (>50%) protection from atherosclerotic lesion formation in these genetically susceptible apoE-knockout mice. A significant but less dramatic reduction in plaquing was observed in mice immunized with PPD.

Example III

Figure 1:
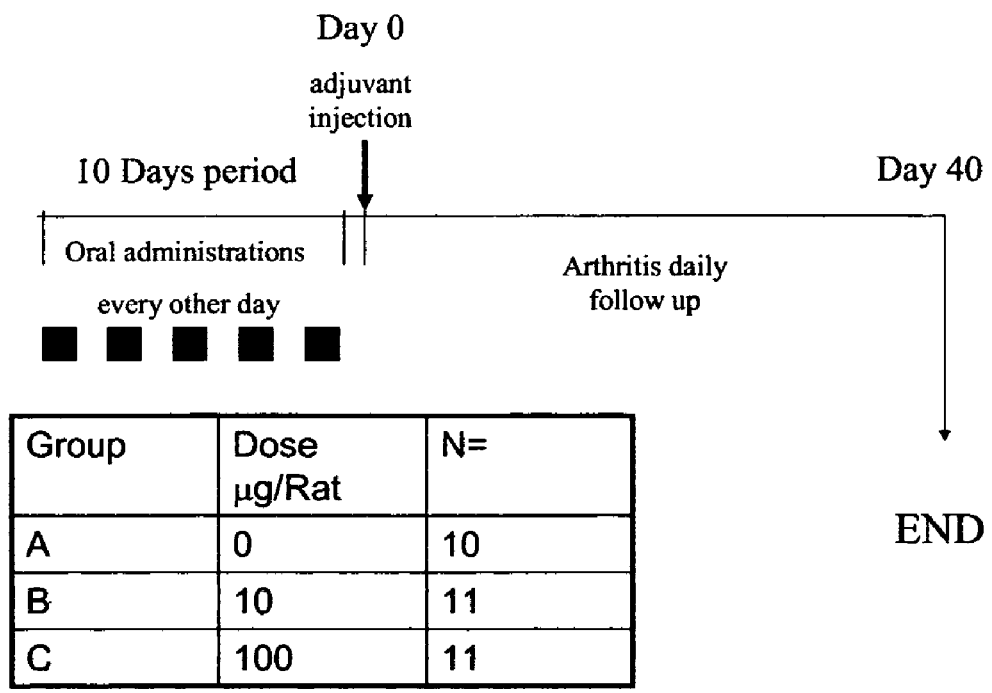
FIG. 1 is a flow chart depicting the synthesis of 2,5' Aldehyde lecitin ether, 1-hexadecyl-2-(5'-oxo-pentanyl)-sn-glycero-3-phosphocholine (for D-ALLE) or 3-hexadecyl-2-(5'-oxo-pentanyl)-sn-glycero-1-phosphocholine (for L-ALLE) (ALLE), according to the synthesis method of the present invention.

Inhibition of Atherogenesis in Genetically Predisposed (ApoE-knockout) Mice by Induction of Oral Tolerance with L-ALLE and D-ALLE Intraperitoneal immunization with the ester analogs of plaque lesion components was effective in inhibiting atherogenesis in apoE-knockout mice (FIG. 1). Thus, the ability of L- and D-ALLE to suppress atherogenesis through oral tolerance was investigated. 34 male 8-10 week old Apo E knock out mice were divided into three groups. In group A (n=11) oral tolerance was induced by administration by gavage of L-ALLE+D-ALLE suspended in PBS (1 mg/mouse) for 5 days every other day. In group B (n=11) mice received 10 µg/mouse L-ALLE+D-ALLE suspended in PBS for 5 days every other day. (0.2 ml/mouse). Mice in group C (n=12) received PBS (containing the same volume of ethanol as in groups A+B). Mice were bled prior to feeding (Time 0) and at the conclusion of the experiment (End) for determination of lipid profile. Atherosclerosis was assessed in heart, aorta, and serum as described above 8 weeks after the last feeding. Mice were weighed every 2 weeks during the experiment. All mice were fed normal chow-diet containing 4.5% fat by weight (0.02% cholesterol) and water ad libitum.

TABLE 2

Inhibition of atherogenesis in apoE-knock out mice by oral administration of L-ALLE and D-ALLE

| Groups | | PBS N = 12 | 1 mg ALLE N = 11 | 10 µg ALLE N = 11 | Statistics |
|---|---|---|---|---|---|
| Time 0 | Weight | 20.7 ± 0.6 | 21.5 ± 0.8 | 21.1 ± 0.8 | P = 0.794 |
| | Chol | 373 ± 25 | 379 ± 23 | 378 ± 31 | P = 0.983 |
| | TG | 128 | 98 | 90 | P = 0.829 |
| End | Weight | 27.3 ± 0.4 | 27.4 ± 0.5 | 24.1 ± 0.8 | P < 0.001 |
| | Chol | 303 ± 17 | 249 ± 24 | 321 ± 15 | P = 0.031 |
| | TG | 81 ± 4 | 78 ± 8 | 93 ± 6 | P = 0.146 |
| | Lesion size ($\mu m^2$) | 176000 ± 13735 | 85278 ± 11633 | 103889 ± 14320 | P < 0.001 |
| | TGF-β pmol/ml | 14696 ± 1352 | 13388 ± 1489 | 18010 ± 1373 | P = 0.07 |

Note:
"Weight" is weight in grams; "Chol" is serum cholesterol and "TG" is serum triglycerides, expressed in mg/dL.

Figure 4:
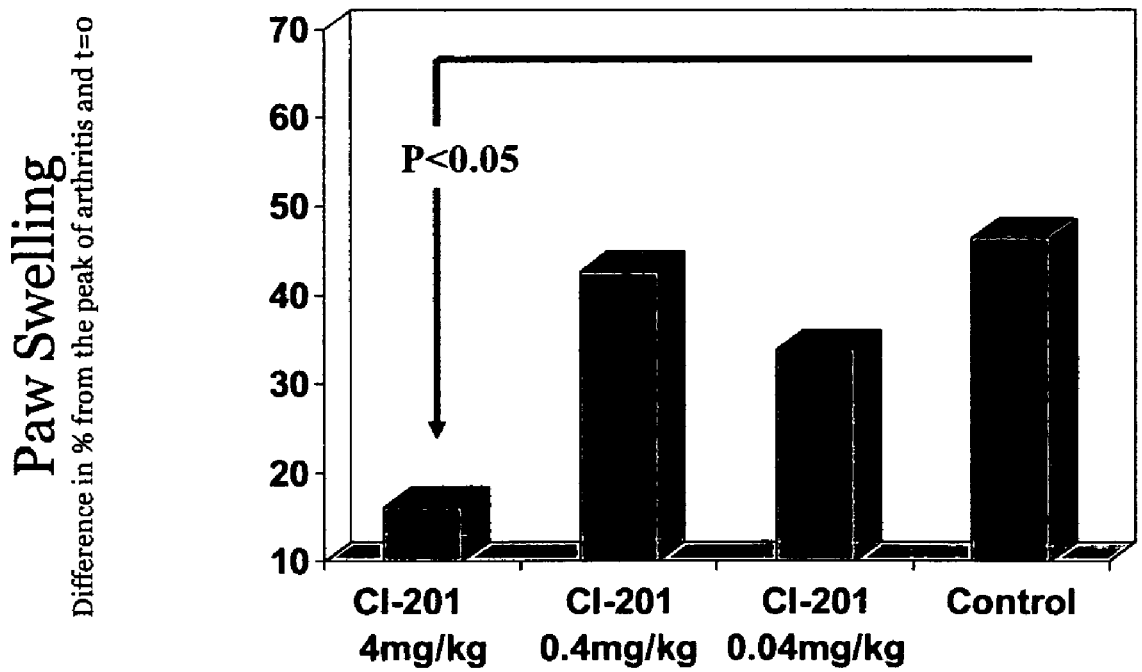
FIG. 4 is a graphic representation demonstrating inhibition of early atherogenesis in apoE-knock out mice by oral tolerance induced by feeding ALLE. 6-7.5 week old apo-E knock out mice were fed mixed D- and L-isomers of ALLE: 10

As can be seen from FIG. 4, the results depicted in Table 2 demonstrate a striking attenuation of atherosclerotic progression measured in the tissues of mice fed low doses (10 µg-1 mg/mouse) of ALLE, compared to unexposed control mice. No significant effect is apparent on other parameters measured, such as weight gain, triglyceride or cholesterol blood levels, or immune competence, as measured by the levels of the immunosuppressive cytokine TGF-β. Thus, the synthetic oxidized LDL component ALLE is a potent inducer of oral tolerance, conferring significant (>50%) protection from atherosclerosis in these genetically susceptible apoE-knock out mice, similar to the protection achieved with peritoneal immunization (see FIG. 1).

Example IV

Inhibition of Atherogenesis in Genetically Predisposed (ApoE-Knock Out) Mice by Induction of Oral and Nasal Tolerance with L-ALLE Mechanisms of mucosal tolerance are active in the nasal mucosa as well as the gut. Thus, nasal exposure and oral exposure to L- and D-ALLE were compared for their effectiveness in suppressing atherogenesis in apoE-knockout mice. 34 male 7-10 weeks old Apo E knock out mice were divided into 3 groups. In group A (n=11) oral tolerance was induced by administration by gavage of L-ALLE suspended in PBS (1 mg/mouse/0.2 ml) for 5 days every other day. In group B (n=11) nasal tolerance was induced as described in Materials and Methods by administration of 10 µg/mouse/10 µl L-ALLE suspended in PBS every other day for 3 days. Mice in group C (n=12) received PBS administered orally and nasally (containing the same volume of ethanol as in groups A+B). Mice were bled prior to feeding (Time 0) and at the conclusion of the experiment (End) for determination of lipid profile. Atherosclerosis was assessed in heart and aorta as described above, 8 weeks after the last feeding. Mice were weighed every 2 weeks during the experiment. All mice were fed normal chow-diet containing 4.5% fat by weight (0.02% cholesterol) and water ad libitum.

TABLE 3

Inhibition of atherogenesis in apoE- knock out mice by nasal administration of L-ALLE

| Groups | | 1 mg ALLE Oral (N = 11) | 10 µg ALLE Nasal (N = 11) | PBS Oral (N = 12) | Statistics |
|---|---|---|---|---|---|
| Time 0 | Weight | 21.1 ± 0.8 | 21.1 ± 0.7 | 22.1 ± 0.9 | P = 0.624 |
| | Chol | 362 ± 27 | 353 ± 31 | 351 ± 27 | P = 0.952 |
| | TG | 144 | 143 | 138 | P = 0.977 |
| End | Weight | 23.3 ± 1.1 | 24.2 ± 0.2 | 24.0 ± 0.5 | P = 0.558 |
| | Chol | 418 ± 43 | 328 ± 18 | 343 ± 25 | P = 0.084 |
| | TG | 82 ± 7 | 74 ± 6 | 79 ± 5 | P = 0.630 |
| | Lesion size ($\mu m^2$) | 76944 ± 17072 | 82708 ± 10986 | 135455 ± 12472 | P = 0.007 |

Note:
"Weight" is weight in grams; "Chol" is serum cholesterol and "TG" is serum triglycerides, expressed in mg/dL.

As can be seen from FIG. 5, the results depicted in Table 3 demonstrate effective (as effective as oral tolerance) inhibition of atherogenesis measured in the tissues of mice receiving nasal exposure to low doses (10 µg/mouse) of ALLE, compared to unexposed control mice. Induction of nasal tolerance, like oral tolerance, had no significant effect on other parameters measured, such as weight gain, triglyceride or cholesterol blood levels. Thus, the synthetic oxidized LDL component ALLE is a potent inducer of nasal as well as oral tolerance, conferring significant (approximately 50%) protection from atherogenesis in these genetically susceptible apoE-knock out mice, similar to the protection achieved induction of oral tolerance alone.

Example V

Suppression of Specific Anti-ox LDL Immune Reactivity in Genetically Predisposed (ApoE-knock Out) Mice by Oral Administration of L-ALLE or POVPC Tolerance induced by mucosal exposure to oxidized analogs of LDL may be mediated by suppression of specific immune responses to the plaque-related antigens. POVPC (1-Hexadecanoyl-2-(5'-oxo-pentanoyl)-sn-glycerophosphocholine) is a non-ether oxidized LDL analog, which, unlike ALLE is susceptible to breakdown in the liver. Lymphocyte proliferation in response to oral exposure to both POVPC and the more stable analog ALLE was measured in apoE-knock out mice. 8 male, 6 week old ApoE knock out mice were divided into 3 groups. In group A (n=2) oral tolerance was induced with 1 mg/mouse L-ALLE suspended in 0.2 ml PBS, administered by gavage, as described above, every other day for 5 days. In group B (n=3) oral tolerance was induced with 1 mg/mouse POVPC suspended in 0.2 ml PBS, administered per os as described above, every other day for 5 days. The mice in group C (n=3) received oral administration of 200 µl PBS every other day for 5 days. Immune reactivity was stimulated by immunization with Human oxidized LDL as described above in the Materials and Methods section, one day after the last feeding. One week after the immunization lymph nodes were collected for assay of proliferation. All mice were fed normal chow-diet containing 4.5% fat by weight (0.02% cholesterol) and water ad libitum.

TABLE 4

Oral pretreatment with synthetic oxidized LDL (ALLE and POVPC) suppresses immune response to Human ox-LDL in apoE-knock out mice Stimulation Index (SI)

| PBS | POVPC | L-ALLE | statistics |
|---|---|---|---|
| 33.1 ± 6.1 | 10.6 ± 2.3 | 7.3 ± 2.3 | P < 0.01 |
| N = 3 | N = 3 | N = 2 | |
| | −68% | −78% | |

As can be seen from FIG. 6, the results depicted in Table 4 demonstrate significant suppression of immune reactivity to Human oxidized-LDL antigen, measured by inhibition of proliferation in the lymph nodes of apoE-knock out mice. Lymphocytes from mice receiving oral exposure to atherogenesis-inhibiting doses (1 mg/mouse) of ALLE or POVPC showed a reduced stimulation index following immunization with ox-LDL, as compared to control (PBS) mice. Since induction of oral, like nasal, tolerance had no significant effect on other parameters measured, such as weight gain, triglyceride or cholesterol blood levels, or immune competence (see Tables 1, 2 and 3), these results indicate a specific suppression of anti-ox-LDL immune reactivity. Thus, oral administration of the synthetic oxidized LDL component L-ALLE is an effective method of attenuating the cellular immune response to immunogenic and atherogenic plaque components in these genetically susceptible apoE-knock out mice. FIG. 4 also demonstrates a similar, if less effective inhibition of proliferation with oral administration of the less stable synthetic oxidized LDL component POVPC.

Example VI

Inhibition of Atherogenesis in Genetically Predisposed (ApoE-knock Out) Mice by Induction of Oral Tolerance with D- and L-isomers of ALLE, and POVPC Since feeding of ALLE and POVPC was shown to inhibit early atherogenesis and immune reactivity to plaque-related Human LDL antigen, the ability of both D- and L-isomers of the ether LDL analog, and the non-ether analog POVPC to suppress the progression of atherogenesis in older mice was compared. Their effect on the triglyceride and cholesterol fractions of VLDL was also monitored by FPLC. 57 male, 24.5 week old Apo E knock out mice were divided into 5 groups. In group A (n=11) oral tolerance was induced with 1 mg/mouse L-ALLE suspended in 0.2 ml PBS, administered by gavage, as described above, every other day for 5 days. In group B (n=9) oral tolerance was induced with 1 mg/mouse D-ALLE suspended in 0.2 ml PBS, administered per os, as described above, every other day for 5 days. In group C (n=10) oral tolerance was induced with 1 mg/mouse POVPC suspended in 0.2 ml PBS, administered by gavage, as described above, every other day for 5 days. Control group D (n=10) received oral administration of PBS (containing the same volume of ethanol as in groups A, B, C). Base line group was sacrificed on time=0. Oral administration of the tested antigens took place every 4 weeks (5 oral feedings; every other day) starting at 24.5 weeks age, during 12 weeks (3 sets of feedings).

Mice were bled prior to feeding (Time 0), after the $2^{nd}$ set of feeding and at the conclusion of the experiment (End) for determination of lipid profile, lipid fractionation and plasma collection. Atherosclerosis was assessed as described above in the heart and aorta and spleens collected for proliferation assay 12 weeks after the first feeding. Weight was recorded every 2 weeks throughout the experiment. All mice were fed normal chow-diet containing 4.5% fat by weight (0.02% cholesterol) and water ad libitum.

Example VII

Inhibition of Atherogenesis in Genetically Predisposed (ApoE-knock Out) Mice by Induction of Oral Tolerance with CI-201

The ability of a stable form of an etherified phospholipid, the acid derivative of ALLE IC-201, to suppress atherogenesis through oral tolerance was investigated. Male 12 week old ApoE KO mice were divided into two groups. In group A (n=14) oral tolerance was induced by administration by gavage of CI-201 (0.025 mg/dose) suspended in PBS for 8 weeks every day (5 times a week). Mice in group B (n=15) received PBS (control). Atherosclerosis was assessed as described above. All mice were fed normal chow-diet containing 4.5% fat by weight (0.02% cholesterol) and water ad libitum.

As can be seen from FIG. 11, the results demonstrate a striking attenuation of atherosclerotic progression measured in the tissues of mice fed low doses of CI-201, as compared with unexposed control mice (PBS). Aortic sinus lesion in the CI-201 treated group was $125,192\pm19,824$ $\mu m^2$ and in the

TABLE 5

Inhibition of atherogenesis in apoE-knock out mice by oral administration of L-ALLE, D-ALLE and POVPC

| Time point | Parameter tested | PBS (n = 10) | 1 mg L-ALLE (n = 11) | 1 mg D-ALLE (n = 9) | 1 mg POVPC (n = 10) | Base line (t = 0) (n = 8) | statistics |
|---|---|---|---|---|---|---|---|
| 0 | Weight | 28.1 ± 0.5 | 29 ± 0.6 | 29.8 ± 0.7 | 29.6 ± 0.7 | 29.8 ± 1.1 | P = 0.445 |
|  | Cholesterol | 413 ± 27 | 413 ± 23 | 409 ± 28 | 401 ± 21 | 393 ± 16 | P = 0.976 |
|  | Triglyceride | 67 ± 5 | 63 ± 8 | 63 ± 4 | 67 ± 7 | 71 ± 8 | P = 0.946 |
| End | Weight | 28.5 ± 0.6 | 29.7 ± 0.5 | 30.4 ± 0.8 | 29.9 ± 0.5 | — | P = 0.177 |
|  | Cholesterol | 365 ± 15 | 391 ± 18 | 394 ± 15 | 358 ± 28 | — | P = 0.481 |
|  | Triglyceride | 84 ± 4 | 83 ± 4 | 94 ± 4 | 85 ± 3 | — | P = 0.207 |
|  | Sinus Lesion $\mu m^2$ | 369688 ± 32570 | 233056 ± 12746 | 245938 ± 20474 | 245750 ± 20423 | 225,714 ± 5,869 | P < 0.001 |
|  | Aorta lesion (% from total area) | 4.5 | 5.4 | 4.5 | 8.3 | 1.4 | P = 0.002 |

Note:
"Weight" is weight in grams; "Cholesterol" is serum cholesterol and "Triglyceride" is serum triglycerides, expressed in mg/dL.

As can be seen from FIG. 7, the results depicted in Table 5 demonstrate effective inhibition of late stage atherogenesis measured in the tissues of older mice following protracted oral exposure to moderately low doses (1 mg/mouse) of the D- and L-isomers of ALLE, and POVPC compared to PBS-fed control mice. Induction of oral tolerance had no significant effect on other parameters measured, such as weight gain, total triglyceride or cholesterol blood levels. Thus, the synthetic oxidized LDL components D-, L-ALLE and POVPC are individually potent inducers of oral tolerance, conferring nearly complete protection from atheromatous progression (as compared with lesion scores at 24.5 weeks) in these genetically susceptible apoE-deficient mice. Surprisingly, it was observed that the inhibition of atherogenesis by these oxidized LDL analogs is accompanied by a significant reduction in VLDL cholesterol and triglycerides, as measured by FPLC (FIGS. 8 and 9).

control group (PBS treated) was $185,400\pm20,947$ $\mu m^2$, demonstrating a decrease of 33% (P=0.051) of the aortic sinus lesion by oral administration of CI-201 in low dose. IL-10 expression in the aorta was higher by 40% in the CI-201 treated group, as compared with the control group. The elevated expression levels of IL-10 in the target organ, the aorta, support the induction of oral tolerance by CI-201 administration. Thus, the stable synthetic oxidized LDL-201, was also found to be a potent inducer of oral tolerance.

Example VIII

Cytokine Expression in the Aorta of Mice Treated with Oxidized Phospholipids (ALLE, CI-201, Et-acetal, Me-acetal & oxLDL) in ApoE Knock Out Mice The effect of ALLE, CI-201, its corresponding acetal derivatives Et-acetal and Me-acetal (Compounds IIa and IIb, FIG. 10) and oxLDL on cytokine expression in the target organ—the aorta—was evaluated using RT-PCR as described hereinabove. ApoE knock out mice were orally administered with 1 mg/mouse ALLE, 1 mg/mouse CI-201, 1 mg/mouse Et-acetal, 1 mg/mouse Me-acetal, 0.1 mg/mouse oxLDL or 0.2 ml/mouse PBS. Oral administrations took place 5 times every other day. The expression of the anti-inflammatory cytokine IL-10 and the proinflammatory cytokine IFN-γ and IL-12 were determined 8 weeks after final oral administration.

As can be seen in FIGS. 12a and 12b, mice treated with ALLE, CI-201, Et-acetal, Me-acetal and oxLDL showed elevated levels of IL-10 as compared with the control PBS-treated group. As can be seen in FIGS. 12c and 12d, an opposite effect was shown in the expression level of IFN-gamma and IL-12. Reduced expression levels of IFN-gamma was detectable in mice treated with ALLE, CI-201, Me-acetal and oxLDL and reduced levels of IL-12 was detectable in mice treated with ALLE, CI-201, Et-acetal and oxLDL.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

1. Ross R. The pathogenesis of atherosclerosis: a perspective for the 1990s. Nature 1993; 362: 801-809.
2. Wick G, Schett G, Amberger A, Kleindienst R, Xu Q. Is atherosclerosis an immunologically mediated disease? Immunol Today 1995; 16: 27-33.
3. Libby P, Hansson G K. Involvement of the immune system in human atherogenesis: current knowledge and unanswered questions. Lab Invest 1991; 64: 5-15
4. George J, Harats D, Gilburd B, Shoenfeld Y. Emerging cross-regulatory roles of immunity and autoimmunity in atherosclerosis. Immunol Res 15:315-322, 1996.
5. Steinberg D, Parathasarathy S, Carew T E, Khoo J C, Witztum J L. Beyond cholesterol. Modifications of low-density lipoprotein that increase its atherogenicity. N Engl J Med 1989; 320: 915-924.
6. Witztum J. The oxidation hypothesis of atherosclerosis. Lancet 1994; 344: 793-795.
7. Palinski W, Miller E, Witztum J L. Immunization of low density lipoprotein (LDL) receptor-deficient rabbits with homologous malondialdehyde-modified LDL reduces atherogenesis. Proc Natl Acad Sci USA. 1995; 92: 821-825.
8. Ameli S, Hultgardh-Nilsson A, Regnstrom J, Calara F, Yano J, Cercek B, Shah P K, Nilsson J. Effect of immunization with homologous LDL and oxidized LDL on early atherosclerosis in hypercholesterolemic rabbits. Arterioscler Thromb Vasc Biol 1996; 16: 1074-1079.
9. George J, Afek A, Gilburd B, Levy Y, Levkovitz H, Shaish A, Goldberg I, Kopolovic Y, Wick G, Shoenfeld Y, Harats D. Hyperimmunization of ApoE deficient mice with homologous oxLDL suppresses early atherogenesis. Atherosclerosis. 1998; 138: 147-152.
10. Weiner H, Freidman A, Miller A. Oral tolerance: immunologic mechanisms and treatment of animal and human organ specific autoimmune diseases by oral administration of autoantigens. Annu Rev Immunol 1994; 12: 809-837.
11. Plump A S, Smith J D, Hayek T, Aalto-Setala K, Walsh A, Verstuyft J G, Rubin E M, Breslow J L. Severe hypercholesterolemia and atherosclerosis in apolipoprotein-E deficient mice created by homologous recombination in ES cells. Cell 1992; 71: 343-353.
12. Zhang S H, Reddick R L, Piedrahita J A, Maeda N. Spontaneous hypercholesterolemia and arterial lesions in mice lacking apolipoprotein E. Science 1992; 258: 468-471.
13. Palinski W, Ord V A, Plump A S, Breslow J L, Steinberg D, Witztum J L. Apo-E-deficient mice are a model of lipoprotein oxidation in atherogenesis. Demonstration of oxidation-specific epitopes in lesions and high titers of autoantibodies to malondialdehyde-lysine in serum. Arterioscler Thromb 1994; 14: 605-616
14. Roselaar S E, Kakkanathu P X, Daugherty A. Lymphocyte populations in atherosclerotic lesions of apo-E–/– and LDL receptor–/– mice; Decreasing density with disease progression. Arterioscler Thromb Vasc Biol 1996; 16: 1013-1018.
15. Palinski W, Yla-Herttuala S, Rosenfeld M E, Butler S W, Socher S A, Parthasarathy S, Curtiss L K, Witztum J L. Antisera and monoclonal antibodies specific for epitopes generated during oxidative modification of low density lipoprotein. Arteriosclerosis 1990; 10: 325-335.
16. Paigen B, Morrow A, Holmes P A, Mitchell D, Williams R A. Quantitative assessment of atherosclerotic lesions in mice. Atherosclerosis 1987; 68: 231-140
17. Rubin E M. Krauss R M, Spangler E A, Verstuyft J G, Clift S M. Inhibition of early atherogenesis in transgenic mice by human apoplipoprotein A-I. Nature 1991; 353: 265-267.
18. Watson A. D., Leitinger N., Navad M., Faul K. F., Hokko S., Witztum J. L., Palinski W., Schwenke D., Salomon R. G., Sha W., Subbanagounder G., Fogelman M. and Berliner J. A. J. Biol. Chem. 272:13597-13607, 1997.
19. Ou Z., Ogamo A., Guo L., Konda Y., Harigaya Y. and Nakagawa Y. Anal. Biochem. 227: 289-294, 1995.
20. Itabe H., Yamamoto H., Suzuki A., Imanaka T. and Takano T. J. Biol. Chem. 271: 33208-33217, 1996.
21. W. J. Bauman and H. K Mangold J. Org. Chem. 31: 498, 1966.
22. E. Baer and Buchnea JBC. 230, 447, 1958.
23. Halperin G et al Methods in Enzymology 129, 838-846, 1986.
24. Ou Z., Ogamo A., Guo L., Konda Y., Harigaya Y. and Nakagawa Y. Anal. Biochem. 227: 289-294, 1995.

What is claimed is:

1. A method of treating a disease or disorder selected from the group consisting of rheumatoid arthritis, juvenile rheumatoid arthritis and inflammatory bowel disease in a subject in need thereof, the method comprising administering to the subject a therapeutically effective amount of a compound, said compound being selected from the group having a formula:

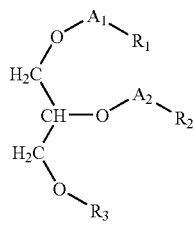

or pharmaceutically acceptable salts thereof, wherein:

(i) $A_1$ and $A_2$ are each independently selected from the group consisting of $CH_2$ and C=O, at least one of $A_1$ and $A_2$ being $CH_2$;

(ii) $R_1$ and $R_2$ are each independently selected from the group consisting of an alkyl chain having 1-27 carbon atoms and

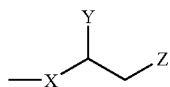

wherein X is an alkyl chain having 1-24 carbon atoms, Y is selected from the group consisting of:

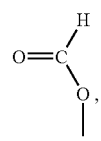

—OH, —H, alkyl, alkoxy halogen, acetoxy and aromatic functional groups; and

Z is selected from the group consisting of:

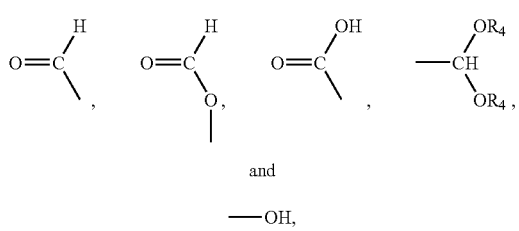

and

—OH, whereas $R_4$ is an alkyl, at least one of $R_1$ and $R_2$ being said

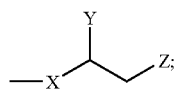

and (iii) $R_3$ is selected from the group consisting of H, acyl, alkyl, phosphocholine, phosphoethanolamine, phosphoserine, phosphocardiolipin and phosphoinositol.

2. The method of claim 1, wherein each of $A_1$ and $A_2$ is $CH_2$.

3. The method of claim 1, wherein $R_1$ is an alkyl chain having 1-27 carbon atoms and $R_2$ is

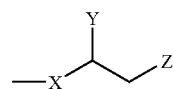

wherein X is an alkyl chain having 1-24 carbon atoms, Y is selected from the group consisting of:

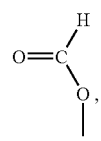

—OH, —H, alkyl, alkoxy halogen, acetoxy and aromatic functional groups; and

Z is selected from the group consisting of:

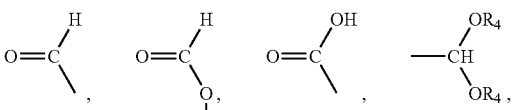

and

—OH, whereas $R_4$ is an alkyl.

4. The method of claim 3, wherein each of $A_1$ and $A_2$ is $CH_2$.

5. The method of claim 1, wherein said compound is administered via mucosal administration.

6. The method of claim 1, wherein administration of said compound is nasal, oral or intra-peritoneal administration.

7. The method of claim 1, wherein administration of said compound reduces immune reactivity to oxidized LDL in said subject.

* * * * *

UNITED STATES PATENT AND TRADEMARK OFFICE
CERTIFICATE OF CORRECTION

| | | |
|---|---|---|
| PATENT NO. | : 7,504,388 B2 | Page 1 of 1 |
| APPLICATION NO. | : 11/183884 | |
| DATED | : March 17, 2009 | |
| INVENTOR(S) | : Harats et al. | |

It is certified that error appears in the above-identified patent and that said Letters Patent is hereby corrected as shown below:

In the Claims

Column 40
Line 63, Claim 1, please replace "bowl" with --bowel--.

Signed and Sealed this
Fifteenth Day of October, 2013

Teresa Stanek Rea
*Deputy Director of the United States Patent and Trademark Office*